US011624076B2

(12) United States Patent
Dubald et al.

(10) Patent No.: US 11,624,076 B2
(45) Date of Patent: Apr. 11, 2023

(54) TAL-EFFECTOR MEDIATED HERBICIDE TOLERANCE

(71) Applicants: BAYER CROPSCIENCE LP, Research Triangle Park, NC (US); Cornell University, Ithaca, NY (US)

(72) Inventors: Manuel Dubald, Raleigh, NC (US); Alain Sailland, Raleigh, NC (US); Yueh-Jiang Hwang, Apex, NC (US); Apurva Bhargava, Apex, NC (US); Adam Bogdanove, Ithaca, NY (US); Fabio Rinaldi, Ithaca, NY (US)

(73) Assignees: BASF Agricultural Solutions Seed US LLC, Florham Park, NJ (US); Cornell University, Ithaca, NY (US)

( * ) Notice: Subject to any disclaimer, the term of this patent is extended or adjusted under 35 U.S.C. 154(b) by 120 days.

(21) Appl. No.: 16/094,685

(22) PCT Filed: Apr. 19, 2017

(86) PCT No.: PCT/US2017/028357
§ 371 (c)(1),
(2) Date: Oct. 18, 2018

(87) PCT Pub. No.: WO2017/184727
PCT Pub. Date: Oct. 26, 2017

(65) Prior Publication Data
US 2019/0119697 A1 Apr. 25, 2019

Related U.S. Application Data

(60) Provisional application No. 62/325,975, filed on Apr. 21, 2016.

(51) Int. Cl.
*C12N 15/82* (2006.01)
*C07K 14/415* (2006.01)

(52) U.S. Cl.
CPC ........ *C12N 15/8274* (2013.01); *C07K 14/415* (2013.01); *C07K 2319/80* (2013.01); *C12N 2310/30* (2013.01)

(58) Field of Classification Search
None
See application file for complete search history.

(56) References Cited

U.S. PATENT DOCUMENTS

| 5,380,831 A * | 1/1995 | Adang | C07K 14/325 536/23.71 |
|---|---|---|---|
| 6,812,010 B1 | 11/2004 | Derose et al. | |
| 9,499,592 B2 | 11/2016 | Zhang et al. | |
| 2012/0270273 A1* | 10/2012 | Zhang | C12P 19/34 435/91.52 |

FOREIGN PATENT DOCUMENTS

| WO | 9638567 A2 | 12/1996 |
|---|---|---|
| WO | 9706269 A1 | 2/1997 |
| WO | 9820144 A2 | 5/1998 |
| WO | 2004024928 A2 | 3/2004 |
| WO | 2011094199 A1 | 8/2011 |
| WO | 2011095460 A1 | 8/2011 |

OTHER PUBLICATIONS

Matringe et al. (2005) Pest Manag Sci 61:269-76.*
Fernandes et al. (2013) "Characterization, modes of action and effects of Trifluralin: a review," Herbicides-current Research and Case Studies in Use, InTech, pp. 489-515.*
"Glycine max chloroplast 4-hydroxyphenylpyruvate dioxygenase long isoform, complete cds, nuclear gene for chloroplast product; and 4-hydroxyphenylpyruvate dioxygenase short isoform mRNA, complete cds", GenBank Accession No. KM460829.1, Apr. 7, 2015.
Bogdanove, AJ, "Principles and applications of TAL effectors for plant physiology and metabolism", Current Opinion in Plant Biology, vol. 19, Jun. 2014, pp. 99-104.
Boch, et al., "Breaking the Code of DNA Binding Specificity of TAL-Type III Effectors", Science, vol. 326, Issue 5959, Dec. 11, 2009, pp. 1509-1512.
Bogdanove, et al., "TAL Effectors: Customizable Proteins for DNA Targeting", Science, vol. 333, Issue 6051, Sep. 30, 2011, pp. 1843-1846.
Bogdanove, et al., "TAL effectors: finding plant genes for disease and defense", Current Opinion in Plant Biology, vol. 13, Issue 4, Aug. 1, 2010, pp. 394-401.
Cermak, et al., "Efficient design and assembly of custom TALEN and other TAL effector-based constructs for DNA targeting", Nucleic Acids Research, vol. 39, Issue 12, Apr. 2011, pp. 1-11.
Crouch, et al., "A mechanistic rationalisation for the substrate specificity of recombinant mammalian 4-hydroxyphenylpyruvate dioxygenase (4-HPPD)", Tetrahedron, vol. 53, Issue 20, May 19, 1997, pp. 6993-7010.
De Lange, et al., "From dead leaf, to new life: TAL effectors as tools for synthetic biology", The Plant Journal, vol. 78, Issue 5, Mar. 2014, p. 753-771.
Doyle, et al., "TAL Effector-Nucleotide Targeter (TALE-NT) 2.0: tools for TAL effector design and target prediction", Nucleic Acids Research, vol. 40, Issue W1, Jul. 2012, pp. W117-W122.
Doyle, et al., "TAL effectors: highly adaptable phytobacterial virulence factors and readily engineered DNA-targeting proteins", Trends in Cell Biology, vol. 23, Issue 8, Aug. 2013, pp. 390-398.

(Continued)

*Primary Examiner* — Russell T Boggs
(74) *Attorney, Agent, or Firm* — Mark S. Scott; BASF Global Intellectual Property

(57) ABSTRACT

The present disclosure relates to methods of altering expression of a genomic locus of interest or specifically targeting a genomic locus of interest in a plant cell, which may involve contacting the genomic locus with a non-naturally occurring or engineered composition that comprises a DNA binding domain comprising one or more Transcription Activator-Like (TAL) effector monomers specifically ordered to target the genomic locus of interest to improve tolerance of the plant cell to an effective concentration of an inhibitor herbicide.

7 Claims, 2 Drawing Sheets

Specification includes a Sequence Listing.

(56) References Cited

OTHER PUBLICATIONS

Dufourmantel, et al., "Generation and characterization of soybean and marker-free tobacco plastid transformants over-expressing a bacterial 4-hydroxyphenylpyruvate dioxygenase which provides strong herbicide tolerance", Plant Biotechnology Journal, vol. 5, Issue 1, Jan. 2007, pp. 118-133.
Fritze, et al., "The Crystal Structures of *Zea mays* and *Arabidopsis* 4-Hydroxyphenylpyruvate Dioxygenase", Plant Physiology, vol. 134, Apr. 2004, pp. 1388-1400.
Gu, et al., "R gene expression induced by a type-III effector triggers disease resistance in rice", Nature, vol. 435, Issue 7045, Jun. 23, 2005, pp. 1122-1125.
International Search Report for PCT Patent Application No. PCT/US2017/28357, dated Jun. 30, 2017, 5 pages.
Jankele, et al., "TAL effectors: tools for DNA Targeting", Briefings in Functional Genomics, vol. 13, Issue 5, Jun. 2014, pp. 409-419.
Kay, et al., "A Bacterial Effector Acts as a Plant Transcription Factor and Induces a Cell Size Regulator", Science, vol. 318, Issue 5850, 2007, pp. 648-651.
Kay, et al., "How Xanthomonas type III effectors manipulate the host plant", Current Opinion in Microbiology, vol. 12, Issue 1, Feb. 2009, pp. 37-43.
Marois, et al., "The Xanthomonas Type III Effector Protein AvrBs3 Modulates Plant Gene Expression and Induces Cell Hypertrophy in the Susceptible Host", Molecular Plant-Microbe Interactions, vol. 15, Issue 7, Jul. 2002, pp. 637-646.
Matringe, et al., "p-Hydroxyphenylpyruvate dioxygenase inhibitor-resistant plants", Pest Management Science, vol. 61, Issue 3, Jan. 4, 2005, pp. 269-276.
Moscou, et al., "A simple cipher governs DNA recognition by TAL effectors", Science, vol. 326, Issue 5959, Dec. 2009, p. 1501.

\* cited by examiner

TAL-EFFECTOR MEDIATED HERBICIDE TOLERANCE

CROSS REFERENCE TO RELATED APPLICATIONS

This application is a National Stage Application of PCT International Application Ser. No. PCT/US2017/028357 filed Apr. 19, 2017 which claims the benefit of U.S. Provisional Application Ser. No. 62/325,975 filed Apr. 21, 2016, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "APA15-6005WOSEQLIST.text sequence listing," created on Apr. 6, 2017, and having a size of 66 kilobytes and is filed concurrently with the specification. The sequence listing contained in this ASCII formatted document is part of the specification and is herein incorporated by reference in its entirety.

FIELD OF THE INVENTION

The present disclosure relates broadly to plant molecular biology, particularly non-naturally occurring or engineered compositions comprising polypeptides that confer improved tolerance in a plant cell or plant tissue to inhibitor herbicides; nucleic acids encoding the same; methods of generating, preparing or constructing said polypeptides and the nucleic acids encoding the same; methods encompassing application of said polypeptides and nucleic acids; host cells, vectors and kits which may comprise said polypeptides and nucleic acids encoding them and uses thereof.

BACKGROUND OF THE INVENTION

TAL effectors are a family of trans-kingdom transcriptional activators that can be readily engineered for highly specific gene targeting (Bogdanove et al., 2010; Cermak et al., 2011). In nature, they are injected into plant cells by plant pathogenic bacteria in the genus *Xanthomonas* to boost the expression of host genes that increase susceptibility to infection. TAL effector-DNA targeting is governed by a simple relationship between an array of repeat sequences in the protein and nucleotides in the target DNA sequence (also called effector binding element, EBE) (Boch et al., 2009; Moscou and Bogdanove, 2009). Each repeat specifies one of the four nucleotides by virtue of a polymorphic pair of amino acids within the repeat, called the repeat variable diresidue (RVD). The string of RVDs determines the sequence of bases (A, C, T, and G) in the EBE. Based on this "code," TAL effector binding sites in a genome can be predicted, EBEs can be synthesized and incorporated into custom gene promoters, and custom TAL effectors can be generated to bind existing DNA sequences of interest. The use of such TAL effectors to modulate the expression of target genes involved in herbicide tolerance has not been described.

SUMMARY OF INVENTION

The compositions and methods of the invention are useful for the production of organisms with enhanced tolerance to inhibitor herbicides. These organisms and compositions comprising the organisms are desirable for agricultural purposes. Methods for conferring herbicide tolerance to a plant are provided, such methods comprising expressing in the plant a nucleic acid molecule comprising a nucleotide sequence encoding a transcription activator-like (TAL) effector which is capable of modulating the expression of an endogenous enzyme in a metabolic pathway that is targeted by the herbicide in the plant, wherein expression of the TAL effector in the plant confers tolerance to the inhibitor herbicide.

In one aspect, the present invention is directed to a method to modulate the expression of a target gene in plant cells, which method comprises providing plant cells with a TAL effector polypeptide according to the invention, said TAL effector being capable of specifically recognizing a target nucleotide sequence, or a complementary strand thereof, within a target gene, and allowing said TAL effector to recognize and particularly bind to said target nucleotide sequence, whereby the expression of said target gene in said plant cells is modulated. In various aspects of the present invention, the target gene is an endogenous plant gene that encodes a protein that is involved in the metabolic pathway that is targeted by one or more inhibitor herbicides in that plant. In specific embodiments, the TAL effector is capable of modulating the expression of one or more enzymes involved in the metabolic pathway depicted in FIG. 1.

In one aspect, the TAL effector comprises at least a repeat domain comprising repeat units, and these repeat units each contain a hypervariable region and each repeat unit is responsible for the recognition of 1 base pair in said target DNA sequence. In a preferred embodiment, all repeat units contain a hypervariable region which determines recognition of base pairs in a target DNA sequence. In specific embodiments, the TAL effector is selected from the group consisting of SEQ ID NO: 1-4, or encodes the amino acid sequence set forth in any of SEQ ID NO:5-8.

The TAL effector can be provided to the plant cells via any suitable methods known in the art. For example, the TAL effector can be exogenously added to the plant cells and the plant cells maintained under conditions such that the TAL effector is introduced into at least one plant cell, binds to the target nucleotide sequence and regulates the expression of the target gene in the plant cells. Alternatively, a nucleotide sequence, e.g., DNA or RNA, encoding the TAL effector polypeptide can be expressed in the plant cells and the plant cells are maintained under conditions such that the expressed polypeptide binds to the target nucleotide sequence and regulates the expression of the target gene in the plant cells.

Any target nucleotide sequence can be modulated by the present method. For example, the target nucleotide sequence can be endogenous or exogenous to the target gene. In a specific embodiment, the target nucleotide sequence is endogenous to the plant. The target nucleotide sequence can be located in any suitable place in relation to the target gene. For example, the target nucleotide sequence can be upstream or downstream of the coding region of the target gene. Alternatively, the target nucleotide sequence is within the coding region of the target gene. Preferably, the target nucleotide sequence is or is at least partially within a promoter of a gene.

Any target gene can be modulated by the present method. For example, the target gene can encode a product that affects biosynthesis, modification, cellular trafficking, metabolism or degradation of a peptide, a protein, an oligonucleotide, a nucleic acid, a vitamin, an oligosaccharide, a carbohydrate, a lipid, or a small molecule. Furthermore, TAL effectors can be used to engineer plants for traits such as increased disease resistance, modification of structural and storage polysaccharides, flavors, proteins, and fatty acids, fruit ripening, yield, color, nutritional characteristics, improved storage capability, increased herbicide tolerance, and the like.

Therefore, the invention provides a method of altering the expression of a gene of interest in a target cell, comprising: determining (if necessary) at least part of the DNA sequence of the structural region and/or a regulatory region of the gene of interest; designing a polypeptide including the repeat units modified in accordance with the invention to recognize specific base pairs on the DNA of known sequence, and causing said modified polypeptide to be present in the target cell, (preferably in the nucleus thereof).

Also provided is a method of growing a plant obtainable by any of the preceding methods, comprising the step of applying a chemical (e.g., an inhibitor herbicide) to said plant or substrate wherein said plant is grown, a process of growing a plant in the field comprising the step of applying a chemical compound on a plant obtainable by any of the preceding methods, a process of producing treated seed comprising the step applying a chemical compound on a seed of plant obtainable by any of the preceding methods, and a method for producing feed, food or fiber comprising the steps of providing a population of plants obtainable by any of the preceding methods and harvesting seeds.

DETAILED DESCRIPTION

Overview

Figure 1:
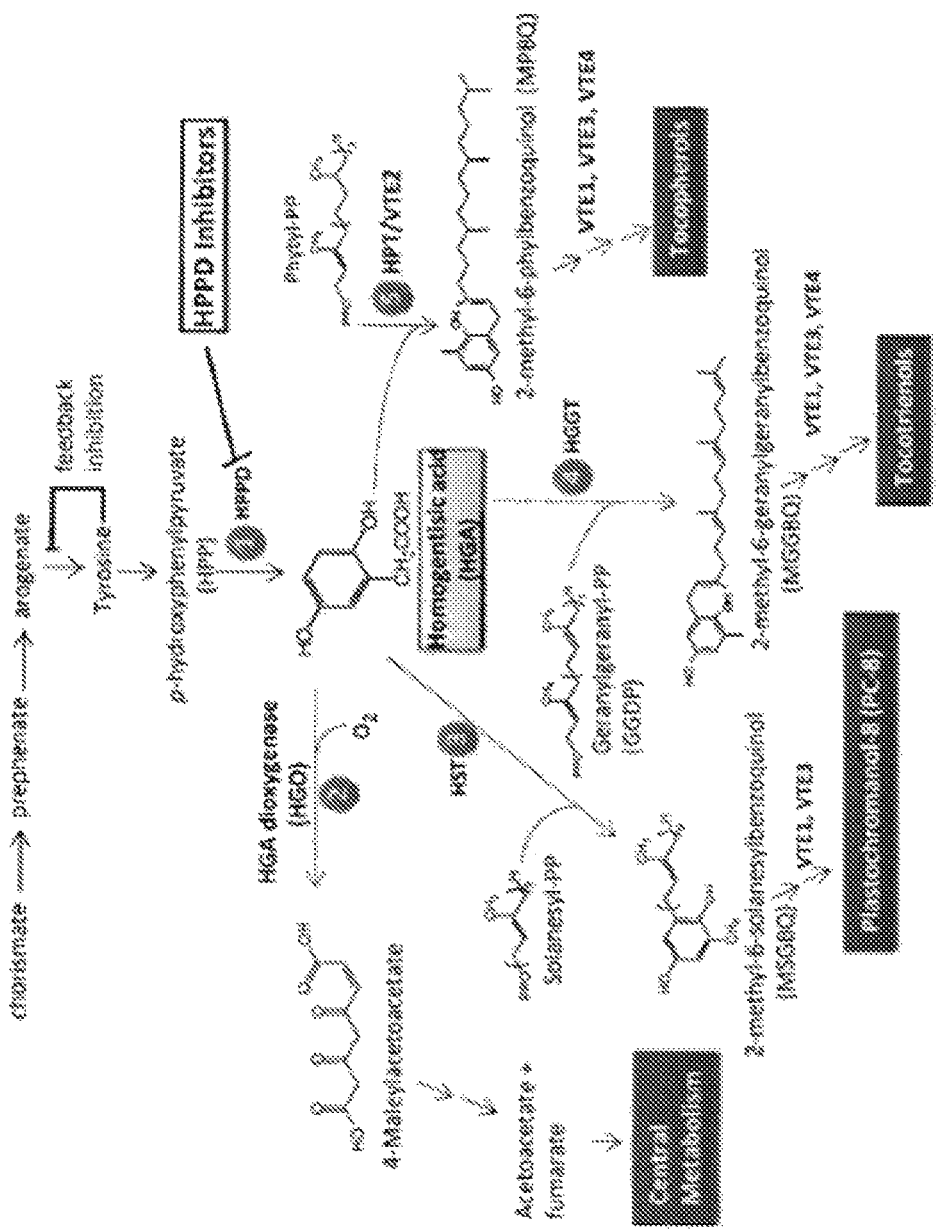
FIG. 1 is a schematic of the HPPD pathway.

Phytopathogenic bacteria of the genus *Xanthomonas* cause severe diseases on many important crop plants. The bacteria translocate an arsenal of effectors including members of the large transcription activator-like (TAL)/AvrB s3-like effector family via the type III secretion system into plant cells (Kay & Bonas Curr. Opin. Microbiol. 2009; 12:37-43, White & Yang Plant Physiol. 2009; 150(4):1677-86; Schornack et al. J. Plant Physiol. 2006; 163:256-272). TAL effectors, key virulence factors of *Xanthomonas*, contain a central domain of tandem repeats, nuclear localization signals (NLSs), and an activation domain (AD) and act as transcription factors in plant cells (Kay et al. Science 2007; 318(5850):648-651; Römer et al. Science 2007; 318(5850): 645-648; Gu et al. Nature 2005; 435(7045):1122-1125). The type member of this effector family, AvrBs3 from *Xanthomonas campestris* pv. *vesicatoria*, contains 17.5 repeats and induces expression of UPA (upregulated by AvrBs3) genes including the Bs3 resistance gene in pepper plants (Kay et al. Science 2007; 318(5850):648-651; Römer et al. Science 2007; 318(5850):645-648; Marois E et al. Mol. Plant-Microbe Interact. 2002; 15(7):637-646). The number and order of repeats in a TAL effector determine its specific activity (Herbers K et al. Nature 1992; 356(6365):172-174). The repeats were shown to be essential for DNA-binding of AvrBs3 and constitute a novel DNA-binding domain (Kay et al. Science 2007; 318(5850):648-651).

TAL effectors contain a central repeat domain containing between 1.5 and 33.5 repeat units that are 33 to 35 and usually 34 amino acid residues in length. The C-terminal repeat unit is generally shorter, and is referred to as a "half repeat" A typical repeat sequence is the 34-mer LTPEQVVAIASHDGGKQALETVQRLLPVLCQAHG (SEQ ID NO:9), but the residues at the 12th and 13th positions ("HD" in SEQ ID NO:9) are hypervariable and are referred to as the repeat variable diresidue (RVD) or the "hypervariable region".

Each RVD is specific to one or more nucleotides, and the combination of repeats in a TAL effector can identify the target sequence. For example, the code between the RVD sequence and the target DNA base can be expressed as NI=A, HD=C, NG=T, NN=R (G or A), NS=N (A, C, G, or T), N*=C, T, A, or G, HG=T, C, or A), HA=C, A, or G, ND=C, NK=G, H*=T, HI=C, HN=G, IG=T, and NA=G.

Transcription activator-like (TAL) effectors could be used to modulate, in plants, other genes related to herbicide tolerance. For example, upregulation of HPPD expression could be combined with upregulation or downregulation of expression of other genes, with the same goal of increased herbicide tolerance.

The TAL effector of the invention can be designed to recognize and bind to the promoter region of a target gene. The recognition site can be within about 20, about 30, about 40, about 50, about 60, about 70, about 100, about 150, about 200, about 250 or about 300 nucleotides of the transcription start site, and/or near a TATA box within the promoter region.

The term "repeat domain" is used to describe the DNA recognition domain from a TAL effector, or artificial version thereof that is made using the methods disclosed, consisting of modular repeat units that when present in a polypeptide confer target DNA specificity. A repeat domain comprised of repeat units can be added to any polypeptide in which DNA sequence targeting is desired and are not limited to use in TAL effectors.

The term "repeat unit" is used to describe the modular portion of a repeat domain from a TAL effector, or an artificial version thereof, that contains one amino acid or two adjacent amino acids that determine recognition of a base pair in a target DNA sequence. Repeat units taken together recognize a defined target DNA sequence and constitute a repeat domain. Repeat units can be added to any polypeptide in which DNA sequence targeting is desired and are not limited to use in TAL effectors.

The term "recognition code" is used to describe the relationship between the amino acids in positions 12 and 13 of a repeat unit and the corresponding DNA base pair in a target DNA sequence that such amino acids confer recognition of, as follows: HD for recognition of C/G; NI for recognition of A/T; NG for recognition of T/A; NS for recognition of C/G or A/T or T/A or G/C; NN for recognition of G/C or A/T; IG for recognition of T/A; N for recognition of C/G; HG for recognition of C/G or T/A; H for recognition of T/A; and NK for recognition of G/C. As used herein, "effector" (or "effector protein" or "effector polypeptide") refers to constructs or their encoded polypeptide products in which said polypeptide is able to recognize a target DNA sequence. The effector protein includes a repeat domain comprised of 1.5 or more repeat units and also may include one or more functional domains such as a regulatory domain. In preferred embodiments of the invention, the "effector" is additionally capable of exerting an effect, such as regulation of gene expression. Although the present invention is not dependent on a particularly biological mechanism, it is believe that the proteins or polypeptides of the invention that recognize a target DNA sequence bind to the target DNA sequence.

The term "naturally occurring" is used to describe an object that can be found in nature as distinct from being produced by man. For example, a polypeptide or polynucleotide sequence that is present in an organism (including viruses) that can be isolated from a source in nature and which has not been intentionally modified by man in the laboratory is naturally occurring. Generally, the term naturally occurring refers to an object as-present in a wild-type individual, such as would be typical for the species.

The terms "modulating expression" "inhibiting expression" and "activating expression" of a gene refer to the ability of a polypeptide of the present invention to affect, inhibit, or activate (respectively) transcription of a gene. Activation includes prevention of subsequent transcriptional inhibition (i.e., prevention of repression of gene expression) and inhibition includes prevention of subsequent transcriptional activation (i.e., prevention of gene activation). Modulation can be assayed by determining any parameter that is indirectly or directly affected by the expression of the target gene. Such parameters include, e.g., changes in RNA or protein levels, changes in protein activity, changes in product levels, changes in downstream gene expression, changes in reporter gene transcription (luciferase, CAT, beta-galactosidase, GFP (see, e.g., Mistili & Spector (1997) Nature Biotechnology 15:961-964); changes in signal transduction, phosphorylation and dephosphorylation, receptor-ligand interactions, second messenger concentrations (e.g., cGMP, cAMP, IP3, and Ca2+), cell growth, neovascularization, in vitro, in vivo, and ex vivo. Such functional effects can be measured by any means known to those skilled in the art, e.g., measurement of RNA or protein levels, measurement of RNA stability, identification of downstream or reporter gene expression, e.g., via chemiluminescence, fluorescence, calorimetric reactions, antibody binding, inducible markers, ligand binding assays; changes in intracellular second messengers such as cGMP and inositol triphosphate (IP3); changes in intracellular calcium levels; cytokine release, and the like.

As used herein, "gene" refers to a nucleic acid molecule or portion thereof which comprises a coding sequence, optionally containing introns, and control regions which regulate the expression of the coding sequence and the transcription of untranslated portions of the transcript. Thus, the term "gene" includes, besides coding sequence, regulatory sequence such as the promoter, enhancer, 5' untranslated regions, 3' untranslated region, termination signals, poly adenylation region and the like. Regulatory sequence of a gene may be located proximal to, within, or distal to the coding region.

As used herein, "target gene" refers to a gene whose expression is to be modulated (i.e., activated or inhibited) by a polypeptide of the present invention.

As used herein, "modulate the expression of a target gene in plant cells" refers to increasing (activation) or decreasing (repression) the expression of the target gene in plant cells with a polypeptide of the present invention, alone or in combination with other transcription and/or translational regulatory factors, or nucleic acids encoding such polypeptide, in plant cells. As used herein, a "target DNA sequence" refers to a portion of double-stranded DNA to which recognition by a protein is desired. In one embodiment, a "target DNA sequence" is all or part of a transcriptional control element for a gene for which a desired phenotypic result can be attained by altering the degree of its expression. A transcriptional control element includes positive and negative control elements such as a promoter, an enhancer, other response elements, e.g., steroid response element, heat shock response element, metal response element, a repressor binding site, operator, and/or a silencer. The transcriptional control element can be viral, eukaryotic, or prokaryotic. A "target DNA sequence" also includes a downstream or an upstream sequence which can bind a protein and thereby modulate transcription.

The use of the term "DNA" or "DNA sequence" herein is not intended to limit the present invention to polynucleotide molecules comprising DNA. Those of ordinary skill in the art will recognize that the methods and compositions of the invention encompass polynucleotide molecules comprised of deoxyribonucleotides (i.e., DNA), ribonucleotides (i.e., RNA) or combinations of ribonucleotides and deoxyribonucleotides. Such deoxyribonucleotides and ribonucleotides include both naturally occurring molecules and synthetic analogues including, but not limited to, nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The polynucleotide molecules of the invention also encompass all forms of polynucleotide molecules including, but not limited to, single-stranded forms, double-stranded forms, hairpins, stem-and-loop structures, and the like.

Furthermore, it is understood by those of ordinary skill in the art that the DNA sequences disclosed herein also encompasses the complement of that exemplified nucleotide sequence. As used herein, "specifically binds to a target DNA sequence" means that the binding affinity of a polypeptide of the present invention to a specified target DNA sequence is statistically higher than the binding affinity of the same polypeptide to a generally comparable, but non-target DNA sequence. It also refers to binding of a repeat domain of the present invention to a specified target DNA sequence to a detectably greater degree, e.g., at least 1.5-fold over background, than its binding to non-target DNA sequences and to the substantial exclusion of non-target DNA sequences. A polypeptide of the present invention's Kd to each DNA sequence can be compared to assess the binding specificity of the polypeptide to a particular target DNA sequence.

As used herein, a "target DNA sequence within a target gene" refers to a functional relationship between the target DNA sequence and the target gene in that recognition of a polypeptide of the present invention to the target DNA sequence will modulate the expression of the target gene. The target DNA sequence can be physically located anywhere inside the boundaries of the target gene, e.g., 5' ends, coding region, 3' ends, upstream and downstream regions outside of cDNA encoded region, or inside enhancer or other regulatory region, and can be proximal or distal to the target gene.

As used herein, "repression" refers to inhibition of transcription or translation by binding of repressor protein to specific site on DNA or mRNA. Preferably, repression includes a significant change in transcription or translation level of at least 1.5 fold, more preferably at least two fold, and even more preferably at least five fold.

As used herein, "activation" refers to enhancement of transcription or translation by binding of activator protein to specific site on DNA or mRNA. Preferably, activation includes a significant change in transcription or translation level of at least 1.5 fold, more preferably at least two fold, and even more preferably at least five fold.

As used herein, "hypervariable region" is meant to mean positions 12 and 13 or equivalent position in a repeat unit of the present invention. It is recognized that positions 12 and 13 of the invention correspond to positions 12 and 13 in the full-length repeat units of AvrBs3 and other TAL effectors as disclosed herein. It is further recognized that by "equivalent positions" is meant positions that correspond to positions 12 and 13, respectively, in a repeat unit of the present disclosure. One can readily determine such equivalent positions by aligning any repeat unit with a full-length repeat unit of AvrBs3.

HPPD Inhibitor Herbicide Tolerance

In various embodiments of the present invention, the TAL effector encompassed herein is capable of binding to and modulating the expression of one or more genes involved in the HPPD inhibitor pathway (FIG. 1). The 4-hydroxyphenylpyruvate dioxygenases (HPPDs) are enzymes which catalyze the reaction in which para-hydroxyphenylpyruvate (abbreviated herein as HPP), a tyrosine degradation product, is transformed into homogentisate (abbreviated herein as HG), the precursor in plants of tocopherol and plastoquinone (Crouch N. P. et al. (1997), Tetrahedron, 53, 20, 6993-7010, Fritze et al. (2004), Plant Physiology 134:1388-1400). Tocopherol acts as a membrane-associated antioxidant. Plastoquinone, firstly acts as an electron carrier between PSII and the cytochrome b6/f complex and secondly, is a redox cofactor for phytoene desaturase, which is involved in the biosynthesis of carotenoids.

Inhibition of HPPD leads to uncoupling of photosynthesis, deficiency in accessory light-harvesting pigments and, most importantly, to destruction of chlorophyll by UV-radiation and reactive oxygen species (bleaching) due to the lack of photo protection normally provided by carotenoids (Norris et al. (1995), Plant Cell 7: 2139-2149). Bleaching of photosynthetically active tissues leads to growth inhibition and plant death.

Thus, in some embodiments, the TAL effector is capable of binding to and modulating the expression of the native HPPD gene in a plant. In specific embodiments, the TAL effector of the invention is capable of increasing the expression of the native HPPD gene in a plant. Representative TAL effectors are set forth herein in SEQ ID NO: 1-8.

Some molecules which inhibit HPPD, and which inhibit transformation of the HPP into homogentisate while binding specifically to the enzyme, have proven to be very effective herbicides.

Besides the attempt of by-passing HPPD-mediated production of homogentisate (U.S. Pat. No. 6,812,010), over-expressing the sensitive enzyme so as to produce quantities of the target enzyme in the plant which are sufficient in relation to the herbicide has been performed (WO96/38567). Overexpression of HPPD resulted in better pre-emergence tolerance to the diketonitrile derivative (DKN) of isoxaflutole (IFT), but the tolerance level was not sufficient for tolerance to post-emergence treatment (Matringe et al. (2005), Pest Management Science 61: 269-276).

In WO2004/024928, the inventors sought to increase the prenylquinone biosynthesis (e.g., synthesis of plastoquinones, tocopherols) in the cells of plants by increasing the flux of the HPP precursor into the cells of these plants. This has been done by connecting the synthesis of said precursor to the "shikimate" pathway by overexpression of a prephenate dehydrogenase (PDH) enzyme. They have also noted that the transformation of plants with a gene encoding a PDH enzyme and a gene encoding an HPPD enzyme makes it possible to increase the tolerance of said plants to HPPD inhibitors.

Further, in US2011/0173718, a method to generate plants tolerant to HPPD inhibitors by overexpressing not only a gene coding for a tolerant HPPD, as for example from *Avena sativa*, but also in combination with several plant genes coding for an HST (homogentisate solanesyltransferase) protein is disclosed. However, the level of tolerance to some selected HPPD inhibitor herbicides was rather limited.

In WO2011/094199 and US2011/0185444, the tolerance of several hundred of soybean wild type lines to the HPPD inhibitor isoxaflutole was evaluated. Very few lines displayed reasonable level of tolerance to the herbicides. The putative QTL (quantitative trait loci) responsible for the tolerance was identified. In this region of the genome, a gene coding for an ABC transporter was identified as being the main trait responsible for the improved tolerance to the HPPD inhibitor herbicide observed. However, transgenic plants expressing the identified genes did not display any improvement in tolerance to the tested HPPD inhibitor herbicides. Compositions also comprise transformed plants, plant cells, tissues, and seeds that are tolerant to the HPPD inhibitor herbicides by the introduction of the nucleic acid sequence of the invention into the genome of the plants, plant cells, tissues, and seeds. The introduction of the sequence allows for HPPD inhibitor herbicides to be applied to plants to selectively kill HPPD inhibitor sensitive weeds or other untransformed plants, but not the transformed organism. The sequences can additionally be used as a marker for selection of plant cells growing in the presence of one or more HPPD inhibitor herbicides.

Despite these successes obtained for the development of plants showing tolerance to several HPPD inhibitors herbicides described above, it is still necessary to develop and/or improve the tolerance of plants to newer or to several different HPPD inhibitors, particularly HPPD inhibitors belonging to the classes of the triketones (e.g. sulcotrione, mesotrione, tembotrione, benzobicyclon and bicyclopyrone), the pyrazolinates (e.g., topramezone and pyrasulfotole), N-(1,2,5-Oxadiazol-3-yl)benzamides (WO2011/035874), N-(tetrazol-4-yl)- or N-(triazol-3-yl)arylcarboxamides (WO2012/028579), pyridazinone derivatives (WO2013/050421 and WO2013/083774); substituted 1,2,5-oxadiazoles (WO2013/072300 and WO2013/072402); and oxoprazin derivatives (WO2013/054495).

Thus, the present invention provides improved compositions and methods for regulating HPPD inhibitor herbicide tolerance. HPPD inhibitor herbicides like those of the class of N (1,2,5-oxadiazol-3-yl)benzamides; N-(tetrazol-4-yl)- or N-(triazol-3-yl)arylcarboxamides, such as 2-chloro-3-ethoxy-4-(methylsulfonyl)-N-(1-methyl-1H-tetrazol-5-yl) benzamide and 2-Chloro-3-(methoxymethyl)-4-(methylsulfonyl)-N-(1-methyl-1H-tetrazol-5-yl)benzamide; N-(1,3, 4-oxadiazol-2-yl)benzamides, such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, such as 2-chloro-3-ethoxy-4-(methylsulfonyl)-N-(1-methyl-1H-tetrazol-5-yl) benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H- tetrazol-5-yl)-4-(trifluoromethyl)benzamide (Cmpd. 4), 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, such as tembotrione, sulcotrione and mesotrione; the class of isoxazoles such as isoxaflutole; or of the class of pyrazolinates, such as pyrasulfotole and topramezone, have an outstanding herbicidal activity against a broad spectrum of economically important monocotyledonous and dicotyledonous annual harmful plants.

Methods for Measuring Inhibitor Herbicide Tolerance

Any suitable method for measuring tolerance to inhibitor herbicides can be used to evaluate the TAL effectors of the invention. Tolerance can be measured by monitoring the ability of a cell or organism to survive a particular inhibitor herbicide application, or the ability to carry out essential cellular functions such as photosynthesis, protein synthesis or respiration and reproduction in a manner that is not readily discernable from untreated cells or organisms, or the ability to have no significant difference in yield or even improved yield for plants treated with inhibitor herbicide compared to such plants not treated with such herbicide (but where weeds have been removed or prevented by a mechanism other than application of the nhibitor herbicide). In some embodiments, tolerance can be measured according to a visible indicator phenotype of the cell or organism transformed with a nucleic acid construct of the invention in the presence of different concentrations of the various HPPD inhibitors. Dose responses and relative shifts in dose responses associated with these indicator phenotypes (formation of brown color, growth inhibition, bleaching, herbicidal effect, etc) are conveniently expressed in terms, for example, of GR50 (concentration for 50% reduction of growth) or MIC (minimum inhibitory concentration) values where increases in values correspond to increases in inherent tolerance of the expressed HPPD, in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance to the inhibitor herbicide. Herbicides can suitably be applied pre-emergence or post emergence.

In various embodiments, tolerance level can be screened via transgenesis, regeneration, breeding and spray testing of a test plant such as tobacco, or a crop plant such as soybean, corn, or cotton. In line with the results obtained by such screening, such plants are more tolerant, desirably tolerant to at least 2 times the normal dose recommended for field applications, even more preferably tolerant up to 4 times the normal dose recommended for field applications, to inhibitor herbicides than such plants that do not contain the TAL effector, or than plants that contain a nucleic acid encoding a different TAL effector, under control of the same promoter as the nucleic acid encoding the TAL effector of the invention. Accordingly, the term "capable of increasing the tolerance of a plant to at least one herbicide" denotes a tolerance by the plant expressing the TAL effector of the invention to at least 1×, 2×, or 3×, or 4×, or greater, the normal field dose of the inhibitor herbicide as compared to a plant that do not contain the TAL effector of the invention, or than plants that contain a nucleic acid encoding a different (e.g., reference) TAL effector.

Polynucleotide Constructs

The TAL effector identified herein may be provided in expression cassettes for expression in the plant of interest. A "plant expression cassette" includes a DNA construct, including a recombinant DNA construct, that is capable of resulting in the expression of a polynucleotide in a plant cell. The cassette can include in the 5'-3' direction of transcription, a transcriptional initiation region (i.e., promoter, particularly a heterologous promoter) operably-linked to one or more polynucleotides of interest, and/or a translation and transcriptional termination region (i.e., termination region) functional in plants. The cassette may additionally contain at least one additional polynucleotide to be introduced into the organism, such as a selectable marker gene. Alternatively, the additional polynucleotide(s) can be provided on multiple expression cassettes. Such an expression cassette is provided with a plurality of restriction sites for insertion of the polynucleotide(s) to be under the transcriptional regulation of the regulatory regions.

In a further embodiment, the present invention relates to a chimeric gene comprising a coding sequence comprising the heterologous TAL effector-encoding nucleic acid of the invention operably linked to a plant-expressible promoter and optionally a transcription termination and polyadenylation region. "Heterologous" generally refers to the polynucleotide or polypeptide that is not endogenous to the cell or is not endogenous to the location in the native genome in which it is present, and has been added to the cell by infection, transfection, microinjection, electroporation, microprojection, or the like. By "operably linked" is intended a functional linkage between two polynucleotides. For example, when a promoter is operably linked to a DNA sequence, the promoter sequence initiates and mediates transcription of the DNA sequence. It is recognized that operably linked polynucleotides may or may not be contiguous and, where used to reference the joining of two polypeptide coding regions, the polypeptides are expressed in the same reading frame.

The promoter may be any polynucleotide sequence which shows transcriptional activity in the chosen plant cells, plant parts, or plants. The promoter may be native or analogous, or foreign or heterologous, to the plant host and/or to the DNA sequence of the invention. Where the promoter is "native" or "analogous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds (1987) Nucleic Acids Res. 15:2343-2361. Also, the location of the promoter relative to the transcription start may be optimized. See, e.g., Roberts et al. (1979) Proc. Natl. Acad. Sci. USA, 76:760-764. Many suitable promoters for use in plants are well known in the art.

For instance, suitable constitutive promoters for use in plants include: the promoters from plant viruses, such as the peanut chlorotic streak caulimovirus (PClSV) promoter (U.S. Pat. No. 5,850,019); the 35S promoter from cauliflower mosaic virus (CaMV) (Odell et al. (1985) Nature 313:810-812); promoters of Chlorella virus methyltransferase genes (U.S. Pat. No. 5,563,328) and the full-length transcript promoter from figwort mosaic virus (FMV) (U.S. Pat. No. 5,378,619); the promoters from such genes as rice actin (McElroy et al. (1990) Plant Cell 2:163-171 and U.S. Pat. No. 5,641,876); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730 and U.S. Pat. No. 5,510,474); maize H3 histone (Lepetit et al. (1992) Mol. Gen. Genet. 231:276-285 and Atanassova et al. (1992) Plant J. 2(3):291-300); *Brassica napus* ALS3 (PCT application WO97/41228); a plant ribulose-biscarboxylase/oxygenase (RuBisCO) small subunit gene; the circovirus (AU 689 311) or the Cassava vein mosaic virus (CsVMV, U.S. Pat. No. 7,053,205); and promoters of various *Agrobacterium* genes (see U.S. Pat. Nos. 4,771,002; 5,102,796; 5,182,200; and 5,428,147).

Suitable inducible promoters for use in plants include: the promoter from the ACE1 system which responds to copper (Mett et al. (1993) PNAS 90:4567-4571); the promoter of the maize In2 gene which responds to benzenesulfonamide herbicide safeners (Hershey et al. (1991) Mol. Gen. Genetics 227:229-237 and Gatz et al. (1994) Mol. Gen. Genetics 243:32-38); and the promoter of the Tet repressor from Tn10 (Gatz et al. (1991) Mol. Gen. Genet. 227:229-237). Another inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone (Schena et al. (1991) Proc. Natl. Acad. Sci. USA 88:10421) or the recent application of a chimeric transcription activator, XVE, for use in an estrogen receptor-based inducible plant expression system activated by estradiol (Zuo et al. (2000) Plant J., 24:265-273). Other inducible promoters for use in plants are described in EP 332104, PCT WO 93/21334 and PCT WO 97/06269 which are herein incorporated by reference in their entirety. Promoters composed of portions of other promoters and partially or totally synthetic promoters can also be used. See, e.g., Ni et al. (1995) Plant J. 7:661-676 and PCT WO 95/14098 describing such promoters for use in plants.

In one embodiment of this invention, a promoter sequence specific for particular regions or tissues of plants can be used to express the TAL effector of the invention, such as promoters specific for seeds (Datla, R. et al., 1997, Biotechnology Ann. Rev. 3, 269-296), especially the napin promoter (EP 255 378 A1), the phaseolin promoter, the glutenin promoter, the helianthinin promoter (WO92/17580), the albumin promoter (WO98/45460), the oleosin promoter (WO98/45461), the SAT1 promoter or the SAT3 promoter (PCT/US98/06978).

Use may also be made of an inducible promoter advantageously chosen from the phenylalanine ammonia lyase (PAL), HMG-CoA reductase (HMG), chitinase, glucanase, proteinase inhibitor (PI), PR1 family gene, nopaline synthase (nos) and vspB promoters (U.S. Pat. No. 5,670,349, Table 3), the HMG2 promoter (U.S. Pat. No. 5,670,349), the apple beta-galactosidase (ABG1) promoter and the apple aminocyclopropane carboxylate synthase (ACC synthase) promoter (WO98/45445). Multiple promoters can be used in the constructs of the invention, including in succession.

The promoter may include, or be modified to include, one or more enhancer elements. In some embodiments, the promoter may include a plurality of enhancer elements. Promoters containing enhancer elements provide for higher levels of transcription as compared to promoters that do not include them. Suitable enhancer elements for use in plants include the PClSV enhancer element (U.S. Pat. No. 5,850,019), the CaMV 35S enhancer element (U.S. Pat. Nos. 5,106,739 and 5,164,316) and the FMV enhancer element (Maiti et al. (1997) Transgenic Res. 6:143-156); the translation activator of the tobacco mosaic virus (TMV) described in Application WO87/07644, or of the tobacco etch virus (TEV) described by Carrington & Freed 1990, J. Virol. 64: 1590-1597, for example, or introns such as the adhl intron of maize or intron 1 of rice actin. See also PCT WO96/23898, WO2012/021794, WO2012/021797, WO2011/084370, and WO2011/028914.

Often, such constructs can contain 5' and 3' untranslated regions. Such constructs may contain a "signal sequence" or "leader sequence" to facilitate co-translational or post-translational transport of the peptide of interest to certain intracellular structures such as the chloroplast (or other plastid) or mitochondria. By "leader sequence" is intended any sequence that, when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a polynucleotide located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a polynucleotide located upstream of a coding sequence.

Convenient termination regions are available from the Ti-plasmid of *A. tumefaciens*, such as the octopine synthase and nopaline synthase termination regions. See also Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; Joshi et al. (1987) Nucleic Acid Res. 15:9627-9639; and European Patent Application EP 0 633 317 A1.

In one embodiment, the polynucleotides of interest are targeted to the chloroplast for expression. In this manner, where the polynucleotide of interest is not directly inserted into the chloroplast, the expression cassette will additionally contain a polynucleotide encoding a transit peptide to direct the nucleotide of interest to the chloroplasts. Such transit peptides are known in the art. See, for example, Von Heijne et al. (1991) Plant Mol. Biol. Rep. 9:104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481.

The polynucleotides of interest to be targeted to the chloroplast may be optimized for expression in the chloroplast to account for differences in codon usage between the plant nucleus and this organelle. In this manner, the polynucleotides of interest may be synthesized using chloroplast-preferred codons. See, for example, U.S. Pat. No. 5,380,831, herein incorporated by reference.

This plant expression cassette can be inserted into a plant transformation vector. By "transformation vector" is intended a DNA molecule that allows for the transformation of a cell. Such a molecule may consist of one or more expression cassettes, and may be organized into more than one vector DNA molecule. For example, binary vectors are plant transformation vectors that utilize two non-contiguous DNA vectors to encode all requisite cis- and trans-acting functions for transformation of plant cells (Hellens and Mullineaux (2000) Trends in Plant Science 5:446-451). "Vector" refers to a polynucleotide construct designed for transfer between different host cells. "Expression vector" refers to a vector that has the ability to incorporate, integrate and express heterologous DNA sequences or fragments in a foreign cell.

The plant transformation vector comprises one or more DNA vectors for achieving plant transformation. For example, it is a common practice in the art to utilize plant transformation vectors that comprise more than one contiguous DNA segment. These vectors are often referred to in the art as binary vectors. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "polynucleotide of interest" (a polynucleotide engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker sequence and the sequence of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) Trends in Plant Science, 5:446-451). Several types of *Agrobacterium* strains (e.g., LBA4404, GV3101, EHA101, EHA105, etc.) can be used for plant transformation. The second plasmid vector is not necessary for introduction of polynucleotides into plants by other methods such as microprojection, microinjection, electroporation, polyethylene glycol, etc.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods. See, for example, the methods for transforming plant cells and regenerating plants described in: U.S. Pat. Nos. 4,459,355, 4,536,475, 5,464,763, 5,177,010, 5,187,073, EP 267,159 A1, EP 604 662 A1, EP 672 752 A1, U.S. Pat. Nos. 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253, 5,405,765, EP 442 174 A1, EP 486 233 A1, EP 486 234 A1, EP 539 563 A1, EP 674 725 A1, WO91/02071, WO95/06128, and WO2011/095460, each of which is herein incorporated by reference, particularly with respect to the transformation methods described therein.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grow into mature plants and produce fertile seeds (e.g. Hiei et al. (1994) The Plant Journal 6:271-282; Ishida et al. (1996) Nature Biotechnology 14:745-750). Explants are typically transferred to a fresh supply of the same medium and cultured routinely. A general description of the techniques and methods for generating transgenic plants are found in Ayres and Park (1994) Critical Reviews in Plant Science 13:219-239 and Bommineni and Jauhar (1997) Maydica 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can be used to confirm the presence of the integrated heterologous gene of interest in the genome of transgenic plant.

Generation of transgenic plants may be performed by one of several methods, including, but not limited to, introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) The Plant Journal 6:271-282; Ishida et al. (1996) Nature Biotechnology 14:745-750; Ayres and Park (1994) Critical Reviews in Plant Science 13:219-239; Bommineni and Jauhar (1997) Maydica 42:107-120) to transfer DNA.

Methods for transformation of chloroplasts are known in the art. See, for example, Svab et al. (1990) Proc. Natl. Acad. Sci. USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305.

The plant cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome. In various embodiments, the seed can be coated with at least one fungicide and/or at least one insecticide, at least one herbicide, and/or at least one safener, or any combination thereof.

Evaluation of Plant Transformation

Following introduction of heterologous foreign DNA into plant cells, the transformation or integration of the heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) Molecular Cloning: A Laboratory Manual (Cold Spring Harbor Laboratory Press, Cold Spring Harbor, N.Y.)). PCR is carried out using oligonucleotide primers specific to the gene of interest or *Agrobacterium* vector background, etc.

Plant transformation may be confirmed by Southern blot analysis of genomic DNA (Sambrook and Russell (2001) supra). In general, total DNA is extracted from the transformant, digested with appropriate restriction enzymes, fractionated in an agarose gel and transferred to a nitrocellulose or nylon membrane. The membrane or "blot" can then be probed with, for example, radiolabeled 32P target DNA fragment to confirm the integration of the introduced gene in the plant genome according to standard techniques (Sambrook and Russell, 2001, supra).

In Northern analysis, RNA is isolated from specific tissues of transformant, fractionated in a formaldehyde agarose gel, and blotted onto a nylon filter according to standard procedures that are routinely used in the art (Sambrook and Russell (2001) supra). Expression of RNA encoded by nucleotide sequences of the invention is then tested by hybridizing the filter to a radioactive probe derived from a GDC by methods known in the art (Sambrook and Russell (2001) supra). RNA can also be detected and/or quantified using reverse transcriptase PCR as known in the art (e.g., Green and Sambrook (2012) Molecular Cloning: A Laboratory Manual, 4th Edition, Cold Spring Harbor Laboratory Press, Woodbury, N.Y.).

Western blot, ELISA, lateral flow testing, and biochemical assays and the like may be carried out on the transgenic plants to determine the presence of protein encoded by the herbicide tolerance gene by standard procedures (Sambrook and Russell (2001) supra) using antibodies that bind to one or more epitopes present on the herbicide tolerance protein.

Plants and Plant Parts

By "plant" is intended whole plants, plant organs (e.g., leaves, stems, roots, etc.), seeds, plant cells, propagules, embryos and progeny of the same. Plant cells can be differentiated or undifferentiated (e.g., callus, suspension culture cells, protoplasts, leaf cells, root cells, phloem cells, pollen). The present invention may be used for introduction of polynucleotides into any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, *papaya*, cashew, macadamia, almond, oats, vegetables, ornamentals, and conifers.

Vegetables include, but are not limited to, tomatoes, lettuce, green beans, lima beans, peas, and members of the genus Curcumis such as cucumber, cantaloupe, and musk melon. Ornamentals include, but are not limited to, azalea, *hydrangea*, hibiscus, roses, tulips, daffodils, petunias, carnation, poinsettia, and *chrysanthemum*. Crop plants are also of interest, including, for example, maize, sorghum, wheat, sunflower, tomato, crucifers, peppers, potato, cotton, rice, soybean, sugarbeet, sugarcane, tobacco, barley, oilseed rape, etc.

This invention is suitable for any member of the monocot plant family including, but not limited to, maize, rice, barley, oats, wheat, sorghum, rye, sugarcane, pineapple, yams, onion, banana, coconut, and dates.

Methods for Increasing Plant Yield

Methods for increasing plant yield are provided. The methods comprise providing a plant comprising, or introducing into a plant or plant cell, a polynucleotide comprising a nucleotide sequence encoding a TAL effector of the invention, growing the plant or a seed thereof in a field, and producing a harvest from said plants or seeds. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase.

In specific methods, the plant comprising the TAL effector of the invention is treated with an effective concentration of an inhibitor herbicide, where the herbicide application results in enhanced plant yield relative to the yield of a plant not comprising the TAL effector of the invention when grown under the same conditions.

Methods for conferring herbicide tolerance in a plant or plant part are also provided. In such methods, a nucleotide sequence encoding the TAL effector of the invention is introduced into the plant, wherein expression of the TAL effector results in inhibitor herbicide tolerance. Plants produced via this method can be treated with an effective concentration of an herbicide and display an increased tolerance to the herbicide. An "effective concentration" of an herbicide in this application is an amount sufficient to slow or stop the growth of plants or plant parts that are not naturally tolerant or rendered tolerant to the herbicide.

Methods of Controlling Weeds in a Field

The present invention therefore also relates to a method of controlling undesired plants or for regulating the growth of plants in crops of plants comprising a nucleotide sequence encoding a TAL effector according to the invention, where one or more inhibitor herbicides are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, an effective concentration of one or more inhibitor herbicide(s) can be applied for example pre-planting (if appropriate also by incorporation into the soil), pre-emergence or post-emergence, and may be combined with the application of other herbicides to which the crop is naturally tolerant, or to which it is resistant via expression of one or more other herbicide resistance transgenes. See, e.g., U.S. App. Pub. No. 2004/0058427 and PCT App. Pub. No. WO98/20144. By "effective concentration" is intended the concentration which controls the growth or spread of weeds or other untransformed plants without significantly affecting the inhibitor-tolerant plant or plant seed. Those of skill in the art understand that application of herbicides can take many different forms and can take place at many different times prior to and/or throughout the seed planting and growth process. "Pre-emergent" application refers to a herbicide which is applied to an area of interest (e.g., a field or area of cultivation) before a plant emerges visibly from the soil. "Post-emergent" application refers to a herbicide which is applied to an area after a plant emerges visibly from the soil. In some instances, the terms "pre-emergent" and "post-emergent" are used with reference to a weed in an area of interest, and in some instances these terms are used with reference to a crop plant in an area of interest. When used with reference to a weed, these terms may apply to a particular type of weed or species of weed that is present or believed to be present in the area of interest. "Pre-plant incorporation" of a herbicide involves the incorporation of compounds into the soil prior to planting.

Thus, the present invention comprises a method of controlling weeds in a field comprising planting in a field a plant or a seed thereof comprising a TAL effector of the invention and applying to said plant or area surrounding said plant an effective concentration of one or more inhibitor herbicides.

In one embodiment of this invention, a field to be planted with plants (such as soybean, cotton, corn, or wheat plants, e.g.) containing a TAL effector of the invention, can be treated with an inhibitor herbicide before the plants are planted or the seeds are sown, which cleans the field of weeds that are killed by the inhibitor herbicide, allowing for no-till practices, followed by planting or sowing of the plants in that same pre-treated field later on (burndown application using an inhibitor herbicide). The residual activity of the herbicide will also protect the emerging and growing plants from competition by weeds in the early growth stages. Once the plants have a certain size, and weeds tend to re-appear, an inhibitor herbicide or a mixture of inhibitor herbicides, can be applied as post-emergent herbicide over the top of the plants, when such plants are tolerant to said herbicides.

In another embodiment of this invention, a field in which seeds containing a nucleotide sequence of the invention were sown, can be treated with an inhibitor herbicide before the plants emerge but after the seeds are sown (the field can be made weed-free before sowing using other means, typically conventional tillage practices such as ploughing, chissel ploughing, or seed bed preparation), where residual activity will keep the field free of weeds killed by the herbicide so that the emerging and growing plants have no competition by weeds (pre-emergence application of an HPPD inhibitor herbicide). Once the plants have a certain size, and weeds tend to re-appear, an herbicide or mixture of herbicides can be applied as post-emergent herbicide over the top of the plants, when such plants are tolerant to said herbicides.

In another embodiment of this invention, plants containing a nucleotide sequence of the invention, can be treated with an inhibitor herbicide, over the top of the plants that have emerged from the seeds that were sown, which cleans the field of weeds killed by the inhibitor herbicide, which application can be together with (e.g., in a spray tank mix), followed by or preceded by a treatment with glyphosate or glufosinate as post-emergent herbicide over the top of the plants, when such plants are tolerant to such herbicides.

Examples of individual representatives of the monocotyledonous and dicotyledonous weeds which can be controlled with an inhibitor herbicide include:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Inhibitor herbicides useful in the present invention can be formulated in various ways, depending on the prevailing biological and/or physico-chemical parameters. Examples of possible formulations are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil or water-based dispersions, oil-miscible solutions, capsule suspensions (CS), dusts (DP), seed-dressing products, granules for application by broadcasting and on the soil, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker Küchler, "Chemische Technologie" [Chemical technology], volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schinfeldt, "Grenzflachenaktive Athylenoxidaddukte" [Interface-active ethylene oxide adducts], Wiss. Verlagsgesell., Stuttgart 1976; Winnacker Küchler, "Chemische Technologie" [Chemical technology], volume 7, C. Hanser Verlag Munich, 4th Ed. 1986.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix.

Methods of Introducing Gene of the Invention into Another Plant

Also provided herein are methods of introducing the TAL effector of the invention into another plant. The TAL effector of the invention, or a fragment thereof, can be introduced into second plant by recurrent selection, backcrossing, pedigree breeding, line selection, mass selection, mutation breeding and/or genetic marker enhanced selection.

Thus, in one embodiment, the methods of the invention comprise crossing a first plant comprising a TAL effector sequence of the invention with a second plant to produce F1 progeny plants and selecting F1 progeny plants that are tolerant to an inhibitor herbicide or that comprise the TAL effector of the invention. The methods may further comprise crossing the selected progeny plants with the first plant comprising the TAL effector of the invention to produce backcross progeny plants and selecting backcross progeny plants that are tolerant to inhibitor herbicide or that comprise the TAL effector of the invention. Methods for evaluating inhibitor herbicide tolerance are provided elsewhere herein. The methods may further comprise repeating these steps one or more times in succession to produce selected second or higher backcross progeny plants that are tolerant to an inhibitor herbicide or that comprise the TAL effector of the invention.

Any breeding method involving selection of plants for the desired phenotype can be used in the method of the present invention. In some embodiments, The F1 plants may be self-pollinated to produce a segregating F2 generation. Individual plants may then be selected which represent the desired phenotype (e.g., inhibitor herbicide tolerance) in each generation (F3, F4, F5, etc.) until the traits are homozygous or fixed within a breeding population.

The second plant can be a plant having a desired trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like. The second plant may be an elite event as described elsewhere herein In various embodiments, plant parts (whole plants, plant organs (e.g., leaves, stems, roots, etc.), seeds, plant cells, propagules, embryos, and the like) can be harvested from the resulting cross and either propagated or collected for downstream use (such as food, feed, biofuel, oil, flour, meal, etc).

Methods of Obtaining a Plant Product

The present invention also relates to a process for obtaining a commodity product, comprising harvesting and/or milling the grains from a crop comprising a TAL effector of the invention to obtain the commodity product. Agronomically and commercially important products and/or compositions of matter including but not limited to animal feed, commodities, and plant products and by-products that are intended for use as food for human consumption or for use in compositions and commodities that are intended for human consumption, particularly devitalized seed/grain products, including a (semi-)processed products produced from such grain/seeds, wherein said product is or comprises whole or processed seeds or grain, animal feed, corn or soy meal, corn or soy flour, corn, corn starch, soybean meal, soy flour, flakes, soy protein concentrate, soy protein isolates, texturized soy protein concentrate, cosmetics, hair care products, soy nut butter, natto, tempeh, hydrolyzed soy protein, whipped topping, shortening, lecithin, edible whole soybeans (raw, roasted, or as edamame), soy yogurt, soy cheese, tofu, yuba, as well as cooked, polished, steamed, baked or parboiled grain, and the like are intended to be within the scope of the present invention if these products and compositions of matter contain detectable amounts of the nucleotide and/or amino acid sequences set forth herein as being diagnostic for any plant containing such nucleotide sequences.

The following examples are offered by way of illustration and not by way of limitation.

EXPERIMENTAL EXAMPLES

Example 1. Design of TAL Effectors for Upregulation of Soybean HPPD

Figure 2:
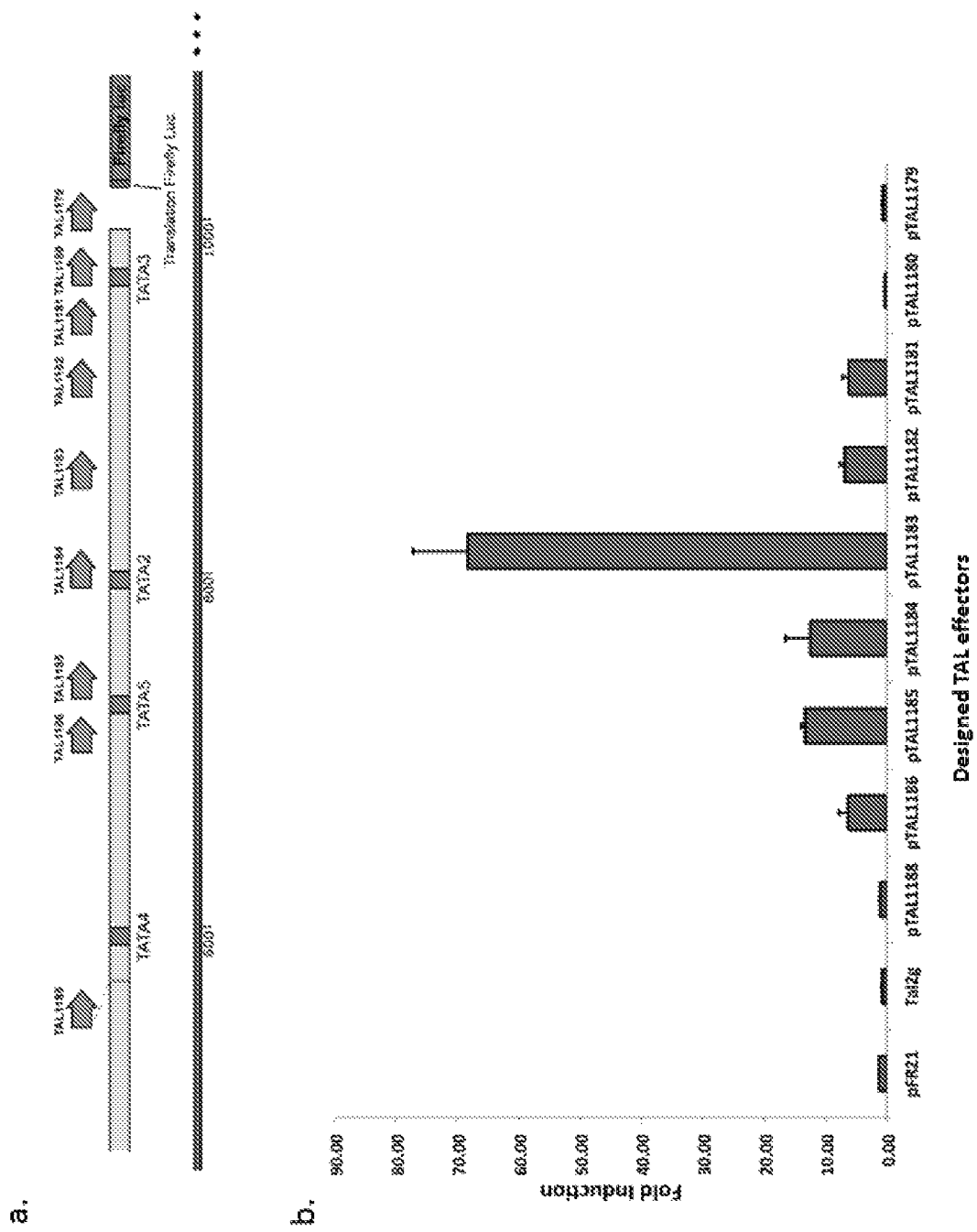
FIG. 2A: Design of the TAL effectors to target the endogeneous HPPD promoter at different regions.
FIG. 2B: TAL effectors were transiently expressed in *N. benthamiania* alongside a using a dual luciferase reporter with the firefly luciferase under the control of the HPPD promoter and the *Renilla* luciferase driven for the 35S promoter as an internal control. Fold induction represents the ratio of Firefly luciferase to *Renilla* luciferase signal amplitude. TAL pFR21 and Tal2 g were used as negative controls.

Various TAL effectors were designed to target the endogenous promoter of the HPPD gene in soybean (HPPD-Gm; GenBank Accession No. KM460829) and validated in a plant transient expression assay system wherein Agrobacterium is used to infiltrate leaves of Nicotiana benthamiana, using reporter genes (FIG. 2A). One of the TAL effectors (TALI 183) resulted in strong activation of the HPPD-Gm promoter (FIG. 2B). Other TAL effectors had a more moderate effect.

Transformation vectors for the TAL effectors were made and introduced into soybean explants. The TAL effector genes resulted in sufficient expression of the HPPD gene to allow for selection of transgenic soybean events using an HPPD inhibitor (tembotrione) for selection.

Molecular analysis performed on the first transgenic events selected with TAL1183 (SEQ ID NO:4, which encodes SEQ ID NO:8) show that there is a strong up-regulation of the expression of the targeted HPPD-Gm gene. This was shown at the mRNA level by RT-qPCR and at the protein level by Western Blot.

Example 2. Soybean Transformation

Soybean transformation is achieved using methods well known in the art, such as the one described using the *Agrobacterium tumefaciens* mediated transformation soybean half-seed explants using essentially the method described by Paz et al. (2006), Plant cell Rep. 25:206. Transformants are identified using tembotrione as selection marker. The appearance of green shoots was observed, and documented as an indicator of tolerance to the herbicide isoxaflutole or tembotrione. The tolerant transgenic shoots will show normal greening comparable to wild-type soybean shoots not treated with isoxaflutole or tembotrione, whereas wild-type soybean shoots treated with the same amount of isoxaflutole or tembotrione will be entirely bleached. This indicates that the presence of the HPPD protein enables the tolerance to HPPD inhibitor herbicides, like isoxaflutole or tembotrione.

Tolerant green shoots are transferred to rooting media or grafted. Rooted plantlets are transferred to the greenhouse after an acclimation period. Plants containing the transgene are then sprayed with HPPD inhibitor herbicides, as for example with tembotrione at a rate of 100 g AI/ha or with mesotrione at a rate of 300 g AI/ha supplemented with ammonium sulfate methyl ester rapeseed oil. Ten days after the application the symptoms due to the application of the herbicide are evaluated and compared to the symptoms observed on wild type plants under the same conditions.

Example 3: Cotton TO Plant Establishment and Selection

Cotton transformation is achieved using methods well known in the art, especially preferred method in the one described in the PCT patent publication WO 00/71733. Regenerated plants are transferred to the greenhouse. Following an acclimation period, sufficiently grown plants are sprayed with HPPD inhibitor herbicides as for example tembotrione equivalent to 100 or 200 gAI/ha supplemented with ammonium sulfate and methyl ester rapeseed oil. Seven days after the spray application, the symptoms due to the treatment with the herbicide are evaluated and compared to the symptoms observed on wild type cotton plants subjected to the same treatment under the same conditions.

Example 4. Transformation of Maize Cells with the Pesticidal Protein Genes Described Herein Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000x Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to the genes of the invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

| DN62A5S Media | | |
|---|---|---|
| Components | Per Liter | Source |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 5. Transformation of Genes of the Invention in Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (22° C. in the dark). After co-cultivation, explants are transferred to recovery period media for 5-10 days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art.

Example 6. Transformation of Rice

Immature rice seeds, containing embryos at the right developmental stage, are collected from donor plants grown under well controlled conditions in the greenhouse. After sterilization of the seeds, immature embryos are excised and preinduced on a solid medium for 3 days. After preinduction, embryos are immersed for several minutes in a suspension of *Agrobacterium* harboring the desired vectors. Then embryos are cocultivated on a solid medium containing acetosyringone and incubated in the dark for 4 days. Explants are then transferred to a first selective medium containing phosphinotricin as selective agent. After approximately 3 weeks, scutella with calli developing were cut into several smaller pieces and transferred to the same selective medium. Subsequent subcultures are performed approximately every 2 weeks. Upon each subculture, actively growing calli are cut into smaller pieces and incubated on a second selective medium. After several weeks calli clearly resistant to phosphinotricin are transferred to a selective regeneration medium. Plantlets generated are cultured on half strength MS for full elongation. The plants are eventually transferred to soil and grown in the greenhouse.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

```
                        SEQUENCE LISTING

<160> NUMBER OF SEQ ID NOS: 10

<210> SEQ ID NO 1
<211> LENGTH: 3696
<212> TYPE: DNA
<213> ORGANISM: Artificial Sequence
<220> FEATURE:
<223> OTHER INFORMATION: pTAL1180

<400> SEQUENCE: 1
ctgaggcaat agctccatca accatgcgag ttcctcttcg ttgaatgccg ggaaatcatc      60
cgctgcccct gcgaaggggt ccgcatcttg ttcccacatc acggtgctgg acgctgccag     120
gtcggcagcc atgggcgtac caggatccgg gaggccgccc cagatcctgg tacgcgggcg     180
ttttaccctc cagctgaggg gcaaatgcag cgcatcgcgc tgttcgggaa cgcgcacctc     240
gacagcctgc tgtgcggagg ggccggtgac agcacgatcc gatcgggacc gtttacggct     300
gcttgcccgc gtctgatctc cctcgtgcat tgggctgggc gcatcaaggt cacgctccag     360
cgaatcggcg aatgcatgca aagacgcctg atccggtgtt tgagctgaag taggggacgg     420 tttggcccctt ttcatccctg atgcctggag gatacggtcc caacgctgcg aggctggggg     480
gagcgttcca ccgcgggctt cgagttcggt gacgcccact ctgcgaaaga gctgtaccaa     540
cccgttcctg ctcatcccga actgcgtcat ggcctcatca aatgcgtacg ctgggtggga     600
gtggcactgg aaaaactcca gcacgcgaac cacttgcgcg tagtcggcaa cgcgatggga     660
cgtgcgttcg ccaatacggc gattgactct tctgatcaat tccggcgcgt gcggcaatcc     720 cttttttcact gcatccatgg caggacgtcc gccgaggcag gccaaggcga cgaggtggtc     780
gttggtcaac gcggccaacg ccggatcagg ccggctcagc tgggccacaa tgctttcgag     840
cgcttgcttg ccgccaatgt tgctggcgat agccaccact tggtccgggg tcaggccatg     900
gtcctggcac agcaccggca acagccgctg caccgtttcg agcgcttgct tgccgccatc     960
gtggctggcg atagccacca cttggtccgg agtcaggcca tggtcctggc acagcaccgg    1020
caacagccgc tgcaccgttt cgagcgcttg cttgccgcca tcgtggctgg cgatagccac    1080
cacttggtcc ggagtcaggc catggtcctg gcacagcacc ggcaacagcc gctgcaccgt    1140
ttcgagcgct tgcttgccgc caatgttgct ggcgatagcc accacttggt ccggggtcag    1200
gccatggtcc tggcacagca ccggcaacag ccgctgcacc gtttcgagcg cttgcttgcc    1260
gccaatgttg ctggcgatag ccaccacttg gtccggggtc aggccatggt cctggcacag    1320
caccggcaac agccgctgca ccgtttcgag cgcttgcttg ccgccatcgt ggctggcgat    1380
agccaccact tggtccggag tcaggccatg gtcctggcac agcaccggca acagccgctg    1440
caccgtttcg agcgcttgct tgccgccaat gttgctggcg atagccacca cttggtccgg    1500
ggtcaggcca tggtcctggc acagcaccgg caacagccgc tgcaccgttt cgagcgcttg    1560
cttgccgcca tcgtggctgg cgatagccac cacttggtcc ggagtcaggc catggtcctg    1620
gcacagcacc ggcaacagcc gctgcaccgt ttcgagcgct tgcttgccgc caccgttgct    1680
```

```
ggcgatagcc accacttggt ccggggtcag gccatggtcc tggcacagca ccggcaacag      1740
ccgctgcacc gtttcgagcg cttgcttgcc gccaatgttg ctggcgatag ccaccacttg      1800
gtccggggtc aggccatggt cctggcacag caccggcaac agccgctgca ccgtttcgag      1860
cgcttgcttg ccgccaccgt tgctggcgat agccaccact tggtccgggg tcaggccatg      1920
gtcctggcac agcaccggca acagccgctg caccgtttcg agcgcttgct tgccgccaat      1980
gttgctggcg atagccacca cttggtccgg ggtcaggcca tggtcctggc acagcaccgg      2040
caacagccgc tgcaccgttt cgagcgcttg cttgccgcca ccgttgctgg cgatagccac      2100
cacttggtcc ggggtcaggc catggtcctg gcacagcacc ggcaacagcc gctgcaccgt      2160
ttcgagcgct tgcttgccgc caatgttgct ggcgatagcc accacttggt ccggggtcag      2220
gccatggtcc tggcacagca ccggcaacag ccgctgcacc gtttcgagcg cttgcttgcc      2280
gccaccgttg ctggcgatag ccaccacttg gtccggggtc aggccatggt cctggcacag      2340
caccggcaac agccgctgca ccgtttcgag cgcttgcttg ccgccaccgt tgctggcgat      2400
agccaccact tggtccgggg tcaggccatg gtcctggcac agcaccggca acagccgctg      2460
caccgtttcg agcgcttgct tgccgccatc gtggctggcg atagccacca cttggtccgg      2520
agtcaggcca tggtcctggc acagcaccgg caacagccgc tgcaccgttt cgagcgcttg      2580
cttgccgcca tcgtggctgg cgatagccac acttggtcc ggagtcaggc catggtcctg      2640
gcacagcacc ggcaacagcc gctgcaccgt ttcgagcgct tgcttgccgc catcgtggct      2700
ggcgatagcc accacttggt ccggagtcag gccatggtcc tggcacagca ccggcaacag      2760
ccgctgcacc gtttcgagcg cttgcttgcc gccatcgtgg ctggcgatag ccaccacttg      2820
gtccggggtc aggttcaggg gggcacccgt cagtgcattg cgcgatgcat gcactgcctc      2880
cattgcggtc acgccgccac gttttgcaat cttcacaagt tggcctgtgt ccaactgtaa      2940
cggcggacct ctcaactccc ccgcatccgt gagcaaggcc tccagggcgc gtgcgccgga      3000
ccactgtttg ccgacgccaa cgatgtcttc gtgtgtcgcc tctggcaacg ccgtgattat      3060
gtgctgatac gtgacagcga cggtccctaa cgctgccggg tgttggctga gcgcaacgat      3120
gtgcgcgtgt gtaaacccat ggcccaccag tgcctcgtgg tgctgcgcca ctgtcgaacg      3180
caccttcggt ttgatcttct cttgctgctg ctgactgtag ccgagcgtgc gtagatccac      3240 ctgcgccggcc ggcgaagcgt cggagggttg cgcagcacgc cgtcgcgggg ccggcttggc      3300
gcgcggcggc cgcgcggcag tgacagcgac acgcacggtg ggtggcgggt catcggctgc      3360
acgcagagcc gattgcgcct catcccactc tgctggggca ccgctgtat gcggcgtgcc      3420 gacggcaggc atcgaatcaa gaagcgatgt atcaagaagc gacggatcga acggacggag      3480
cagatcgctg aagctgcccg ccgagaacgc aggtgagggc gcaggggag atggcagccg      3540 ggtccgggac accgtccgcc gagcgggcaa gccatccaga gggctgccag caggcgcaga      3600 cacccccacga tctgcagtcg gctgaaccct atccggttgg ggtccgggca gaagctcgcg      3660
ggcaggactt ggcctgcgcg gacgaatggg atccat                                3696
```

<210> SEQ ID NO 2
<211> LENGTH: 3696
<212> TYPE: DNA
<213> ORGANISM: Artificial Sequence
<220> FEATURE:
<223> OTHER INFORMATION: pTAL1181

<400> SEQUENCE: 2

| | |
|---|---|
| ctgaggcaat agctccatca accatgcgag ttcctcttcg ttgaatgccg ggaaatcatc | 60 |
| cgctgcccct gcgaaggggt ccgcatcttg ttcccacatc acggtgctgg acgctgccag | 120 |
| gtcggcagcc atgggcgtac caggatccgg gaggccgccc cagatcctgg tacgcgggcg | 180 |
| ttttaccctc cagctgaggg gcaaatgcag cgcatcgcgc tgttcgggaa cgcgcacctc | 240 |
| gacagcctgc tgtgcggagg ggccggtgac agcacgatcc gatcgggacc gtttacggct | 300 |
| gcttgcccgc gtctgatctc cctcgtgcat tgggctgggc gcatcaaggt cacgctccag | 360 |
| cgaatcggcg aatgcatgca aagacgcctg atccggtgtt tgagctgaag tagggacgg | 420 |
| tttggcccctt ttcatccctg atgcctggag gatacggtcc caacgctgcg aggctggggg | 480 |
| gagcgttcca ccgcgggctt cgagttcggt gacgcccact ctgcgaaaga gctgtaccaa | 540 |
| cccgttcctg ctcatcccga actgcgtcat ggcctcatca aatgcgtacg ctgggtggga | 600 |
| gtggcactgg aaaaactcca gcacgcgaac cacttgcgcg tagtcggcaa cgcgatggga | 660 |
| cgtgcgttcg ccaatacggc gattgactct tctgatcaat ccggcgcgt gcggcaatcc | 720 |
| cttttttcact gcatccatgg caggacgtcc gccgaggcag gccaaggcga cgaggtggtc | 780 |
| gttggtcaac gcggccaacg ccggatcagg ccggctcagc tgggccacaa tgctttcgag | 840 |
| cgcttgcttg ccgccaccgt tgctggcgat agccaccact tggtccgggg tcaggccatg | 900 |
| gtcctggcac agcaccggca acagccgctg caccgtttcg agcgcttgct tgccgccgtg | 960 |
| attgctggcg atagccacca cttggtccgg ggtcaggcca tggtcctggc acagcaccgg | 1020 |
| caacagccgc tgcaccgttt cgagcgcttg cttgccgcca atgttgctgg cgatagccac | 1080 |
| cacttggtcc ggggtcaggc catggtcctg gcacagcacc ggcaacagcc gctgcaccgt | 1140 |
| ttcgagcgct tgcttgccgc caatgttgct ggcgatagcc accacttggt ccggggtcag | 1200 |
| gccatggtcc tggcacagca ccggcaacag ccgctgcacc gtttcgagcg cttgcttgcc | 1260 |
| gccatcgtgg ctggcgatag ccaccacttg gtccggagtc aggccatggt cctggcacag | 1320 |
| caccggcaac agccgctgca ccgtttcgag cgcttgcttg ccgccatcgt ggctggcgat | 1380 |
| agccaccact tggtccggag tcaggccatg gtcctggcac agcaccggca acagccgctg | 1440 |
| caccgtttcg agcgcttgct tgccgccaat gttgctggcg atagccacca cttggtccgg | 1500 |
| ggtcaggcca tggtcctggc acagcaccgg caacagccgc tgcaccgttt cgagcgcttg | 1560 |
| cttgccgcca atgttgctgg cgatagccac cacttggtcc ggggtcaggc catggtcctg | 1620 |
| gcacagcacc ggcaacagcc gctgcaccgt ttcgagcgct tgcttgccgc catcgtggct | 1680 |
| ggcgatagcc accacttggt ccggagtcag gccatggtcc tggcacagca ccggcaacag | 1740 |
| ccgctgcacc gtttcgagcg cttgcttgcc gccaccgttg ctggcgatag ccaccacttg | 1800 |
| gtccggggtc aggccatggt cctggcacag caccggcaac agccgctgca ccgtttcgag | 1860 |
| cgcttgcttg ccgccaccgt tgctggcgat agccaccact tggtccgggg tcaggccatg | 1920 |
| gtcctggcac agcaccggca acagccgctg caccgtttcg agcgcttgct tgccgccaat | 1980 |
| gttgctggcg atagccacca cttggtccgg ggtcaggcca tggtcctggc acagcaccgg | 2040 |
| caacagccgc tgcaccgttt cgagcgcttg cttgccgcca tcgtggctgg cgatagccac | 2100 |
| cacttggtcc ggagtcaggc catggtcctg gcacagcacc ggcaacagcc gctgcaccgt | 2160 |
| ttcgagcgct tgcttgccgc caatgttgct ggcgatagcc accacttggt ccggggtcag | 2220 |
| gccatggtcc tggcacagca ccggcaacag ccgctgcacc gtttcgagcg cttgcttgcc | 2280 |
| gccatcgtgg ctggcgatag ccaccacttg gtccggagtc aggccatggt cctggcacag | 2340 |
| caccggcaac agccgctgca ccgtttcgag cgcttgcttg ccgccaccgt tgctggcgat | 2400 |

```
agccaccact tggtccgggg tcaggccatg gtcctggcac agcaccggca acagccgctg    2460
caccgtttcg agcgcttgct tgccgccaat gttgctggcg atagccacca cttggtccgg    2520
ggtcaggcca tggtcctggc acagcaccgg caacagccgc tgcaccgttt cgagcgcttg    2580
cttgccgcca atgttgctgg cgatagccac cacttggtcc ggggtcaggc catggtcctg    2640
gcacagcacc ggcaacagcc gctgcaccgt tcgagcgct tgcttgccgc catcgtggct    2700
ggcgatagcc accacttggt ccggagtcag gccatggtcc tggcacagca ccggcaacag    2760
ccgctgcacc gtttcgagcg cttgcttgcc gccatcgtgg ctggcgatag ccaccacttg    2820
gtccggggtc aggttcaggg gggcacccgt cagtgcattg cgcgatgcat gcactgcctc    2880
cattgcggtc acgccgccac gttttgcaat cttcacaagt tggcctgtgt ccaactgtaa    2940
cggcggacct ctcaactccc ccgcatccgt gagcaaggcc tccagggcgc gtgcgccgga    3000
ccactgtttg ccgacgccaa cgatgtcttc gtgtgtcgcc tctggcaacg ccgtgattat    3060
gtgctgatac gtgacagcga cggtccctaa cgctgccggg tgttggctga gcgcaacgat    3120
gtgcgcgtgt gtaaacccat ggcccaccag tgcctcgtgg tgctgcgcca ctgtcgaacg    3180
caccttcggt ttgatcttct cttgctgctg ctgactgtag ccgagcgtgc gtagatccac    3240
ctgcgcggcc ggcgaagcgt cggagggttg cgcagcacgc cgtcgcgggg ccggcttggc    3300
gcgcggcggc cgcgcggcag tgacagcgac acgcacggtg ggtggcgggt catcggctgc    3360
acgcagagcc gattgcgcct catcccactc tgctgggca gccgctgtat gcggcgtgcc    3420
gacggcagga tcgaatcaa gaagcgatgt atcaagaagc gacggatcga acggacggag    3480
cagatcgctg aagctgcccg ccgagaacgc aggtgagggc gcaggggag atggcagccg    3540 ggtccgggac accgtccgcc gagcgggcaa gccatccaga gggctgccag caggcgcaga    3600
caccccacga tctgcagtcg gctgaaccct atccggttgg ggtccgggca gaagctcgcg    3660
ggcaggactt ggcctgcgcg gacgaatggg atccat                               3696
```

<210> SEQ ID NO 3
<211> LENGTH: 3696
<212> TYPE: DNA
<213> ORGANISM: Artificial Sequence
<220> FEATURE:
<223> OTHER INFORMATION: pTAL1182

<400> SEQUENCE: 3

```
ctgaggcaat agctccatca accatgcgag ttcctcttcg ttgaatgccg ggaaatcatc      60
cgctgcccct gcgaaggggt ccgcatcttg ttcccacatc acggtgctgg acgctgccag     120
gtcggcagcc atgggcgtac caggatccgg gaggccgccc cagatcctgg tacgcgggcg     180 ttttacccctc cagctgaggg gcaaatgcag cgcatcgcg tgttcgggaa cgcgcacctc     240
gacagcctgc tgtgcggagg ggccggtgac agcacgatcc gatcgggacc gtttacggct     300
gcttgcccgc gtctgatctc cctcgtgcat tgggctgggc gcatcaaggt cacgctccag     360
cgaatcggcg aatgcatgca aagacgcctg atccggtgtt tgagctgaag tagggacgg     420 tttggccctt tcatccctg atgcctggag gatacggtcc caacgctgcg aggctggggg     480
gagcgttcca ccgcgggctt cgagttcggt gacgcccact ctgcgaaaga gctgtaccaa     540
cccgttcctg ctcatcccga actgcgtcat ggcctcatca aatgcgtacg ctgggtggga     600
gtggcactgg aaaaactcca gcacgcgaac cacttgcgcg tagtcggcaa cgcgatggga     660
cgtgcgttcg ccaatacggc gattgactct tctgatcaat tccggcgcgt gcggcaatcc     720
```

| | |
|---|---|
| cttttcact gcatccatgg caggacgtcc gccgaggcag gccaaggcga cgaggtggtc | 780 |
| gttggtcaac gcggccaacg ccggatcagg ccggctcagc tgggccacaa tgctttcgag | 840 |
| cgcttgcttg ccgccatcgt ggctggcgat agccaccact tggtccgggg tcaggccatg | 900 |
| gtcctggcac agcaccggca acagccgctg caccgtttcg agcgcttgct tgccgccaat | 960 |
| gttgctggcg atagccacca cttggtccgg ggtcaggcca tggtcctggc acagcaccgg | 1020 |
| caacagccgc tgcaccgttt cgagcgcttg cttgccgcca tcgtggctgg cgatagccac | 1080 |
| cacttggtcc ggagtcaggc catggtcctg gcacagcacc ggcaacagcc gctgcaccgt | 1140 |
| ttcgagcgct tgcttgccgc caccgttgct ggcgatagcc accacttggt ccggggtcag | 1200 |
| gccatggtcc tggcacagca ccggcaacag ccgctgcacc gtttcgagcg cttgcttgcc | 1260 |
| gccaatgttg ctggcgatag ccaccacttg gtccggggtc aggccatggt cctggcacag | 1320 |
| caccggcaac agccgctgca ccgtttcgag cgcttgcttg ccgccatcgt ggctggcgat | 1380 |
| agccaccact tggtccggag tcaggccatg gtcctggcac agcaccggca acagccgctg | 1440 |
| caccgtttcg agcgcttgct tgccgccatc gtggctggcg atagccacca cttggtccgg | 1500 |
| agtcaggcca tggtcctggc acagcaccgg caacagccgc tgcaccgttt cgagcgcttg | 1560 |
| cttgccgcca ccgttgctgg cgatagccac cacttggtcc ggggtcaggc catggtcctg | 1620 |
| gcacagcacc ggcaacagcc gctgcaccgt ttcgagcgct tgcttgccgc catcgtggct | 1680 |
| ggcgatagcc accacttggt ccggagtcag gccatggtcc tggcacagca ccggcaacag | 1740 |
| ccgctgcacc gtttcgagcg cttgcttgcc gccaatgttg ctggcgatag ccaccacttg | 1800 |
| gtccggggtc aggccatggt cctggcacag caccggcaac agccgctgca ccgtttcgag | 1860 |
| cgcttgcttg ccgccatcgt ggctggcgat agccaccact tggtccggag tcaggccatg | 1920 |
| gtcctggcac agcaccggca acagccgctg caccgtttcg agcgcttgct tgccgccaat | 1980 |
| gttgctggcg atagccacca cttggtccgg ggtcaggcca tggtcctggc acagcaccgg | 2040 |
| caacagccgc tgcaccgttt cgagcgcttg cttgccgcca ccgttgctgg cgatagccac | 2100 |
| cacttggtcc ggggtcaggc catggtcctg gcacagcacc ggcaacagcc gctgcaccgt | 2160 |
| ttcgagcgct tgcttgccgc cgtgattgct ggcgatagcc accacttggt ccggggtcag | 2220 |
| gccatggtcc tggcacagca ccggcaacag ccgctgcacc gtttcgagcg cttgcttgcc | 2280 |
| gccaccgttg ctggcgatag ccaccacttg gtccggggtc aggccatggt cctggcacag | 2340 |
| caccggcaac agccgctgca ccgtttcgag cgcttgcttg ccgccaatgt tgctggcgat | 2400 |
| agccaccact tggtccgggg tcaggccatg gtcctggcac agcaccggca acagccgctg | 2460 |
| caccgtttcg agcgcttgct tgccgccatc gtggctggcg atagccacca cttggtccgg | 2520 |
| agtcaggcca tggtcctggc acagcaccgg caacagccgc tgcaccgttt cgagcgcttg | 2580 |
| cttgccgcca tcgtggctgg cgatagccac cacttggtcc ggagtcaggc catggtcctg | 2640 |
| gcacagcacc ggcaacagcc gctgcaccgt ttcgagcgct tgcttgccgc catcgtggct | 2700 |
| ggcgatagcc accacttggt ccggagtcag gccatggtcc tggcacagca ccggcaacag | 2760 |
| ccgctgcacc gtttcgagcg cttgcttgcc gccgtgattg ctggcgatag ccaccacttg | 2820 |
| gtccggggtc aggttcaggg gggcacccgt cagtgcattg cgcgatgcat gcactgcctc | 2880 |
| cattgcggtc acgccgccac gttttgcaat cttcacaagt tggcctgtgt ccaactgtaa | 2940 |
| cggcggacct ctcaactccc ccgcatccgt gagcaaggcc tccagggcgc gtgcgccgga | 3000 |
| ccactgtttg ccgacgccaa cgatgtcttc gtgtgtcgcc tctggcaacg ccgtgattat | 3060 |
| gtgctgatac gtgacagcga cggtccctaa cgctgccggg tgttggctga gcgcaacgat | 3120 |

```
gtgcgcgtgt gtaaacccat ggcccaccag tgcctcgtgg tgctgcgcca ctgtcgaacg    3180
caccttcggt ttgatcttct cttgctgctg ctgactgtag ccgagcgtgc gtagatccac    3240
ctgcgcggcc ggcgaagcgt cggagggttg cgcagcacgc cgtcgcgggg ccggcttggc    3300
gcgcggcggc cgcgcggcag tgacagcgac acgcacggtg ggtggcgggt catcggctgc    3360
acgcagagcc gattgcgcct catcccactc tgctggggca gccgctgtat gcggcgtgcc    3420
gacggcaggc atcgaatcaa gaagcgatgt atcaagaagc gacggatcga acggacggag    3480
cagatcgctg aagctgcccg ccgagaacgc aggtgagggc caggggag atggcagccg       3540 ggtccgggac accgtccgcc gagcgggcaa gccatccaga gggctgccag caggcgcaga    3600
caccccacga tctgcagtcg gctgaaccct atccggttgg ggtccgggca gaagctcgcg    3660
ggcaggactt ggcctgcgcg gacgaatggg atccat                              3696

<210> SEQ ID NO 4
<211> LENGTH: 3696
<212> TYPE: DNA
<213> ORGANISM: Artificial Sequence
<220> FEATURE:
<223> OTHER INFORMATION: pTAL1183

<400> SEQUENCE: 4
ctgaggcaat agctccatca accatgcgag ttcctcttcg ttgaatgccg ggaaatcatc      60
cgctgcccct gcgaaggggt ccgcatcttg ttcccacatc acggtgctgg acgctgccag     120
gtcggcagcc atgggcgtac caggatccgg gaggccgccc cagatcctgg tacgcgggcg     180
ttttaccctc cagctgaggg gcaaatgcag cgcatcgcgc tgttcgggaa cgcgcaccctc    240 gacagcctgc tgtgcggagg ggccggtgac agcacgatcc gatcgggacc gtttacggct     300
gcttgcccgc gtctgatctc cctcgtgcat tgggctgggc gcatcaaggt cacgctccag     360
cgaatcggcg aatgcatgca aagacgcctg atccggtgtt tgagctgaag taggggacgg     420 tttggcccctt ttcatccctg atgcctggag gatacggtcc caacgctgcg aggctggggg    480
gagcgttcca ccgcgggctt cgagttcggt gacgcccact ctgcgaaaga gctgtaccaa    540
cccgttcctg ctcatcccga actgcgtcat ggcctcatca aatgcgtacg ctgggtggga    600
gtggcactgg aaaaactcca gcacgcgaac cacttgcgcg tagtcggcaa cgcgatggga    660
cgtgcgttcg ccaatacggc gattgactct tctgatcaat tccggcgcgt gcggcaatcc    720 cttttttcact gcatccatgg caggacgtcc gccgaggcag gccaaggcga cgaggtggtc    780
gttggtcaac gcgccaacg ccggatcagg ccggctcagc tgggccacaa tgctttcgag     840
cgcttgcttg ccgccaccgt tgctggcgat agccaccact tggtccgggg tcaggccatg    900
gtcctggcac agcaccggca acagccgctg caccgttcg agcgcttgct tgccgccaat    960
gttgctggcg atagccacca cttggtccgg ggtcaggcca tggtcctggc acagcaccgg   1020
caacagccgc tgcaccgttt cgagcgcttg cttgccgcca tcgtggctgg cgatagccac    1080
cacttggtcc ggagtcaggc catggtcctg cacagcaccc ggcaacagcc gctgcaccgt    1140
ttcgagcgct tgcttgccgc caccgttgct ggcgatagcc accacttggt ccggggtcag    1200
gccatggtcc tggcacagca ccggcaacag ccgctgcacc gtttcgagcg cttgcttgcc    1260
gccatcgtgg ctggcgatag ccaccacttg gtccggagtc aggccatggt cctggcacag    1320
caccggcaac agccgctgca ccgtttcgag cgcttgcttg ccgccatcgt ggctggcgat    1380
agccaccact tggtccggag tcaggccatg gtcctggcac agcaccggca acagccgctg    1440
```

```
caccgtttcg agcgcttgct tgccgccacc gttgctggcg atagccacca cttggtccgg    1500
ggtcaggcca tggtcctggc acagcaccgg caacagccgc tgcaccgttt cgagcgcttg    1560
cttgccgccg tgattgctgg cgatagccac cacttggtcc ggggtcaggc catggtcctg    1620
gcacagcacc ggcaacagcc gctgcaccgt ttcgagcgct tgcttgccgc catcgtggct    1680
ggcgatagcc accacttggt ccggagtcag gccatggtcc tggcacagca ccggcaacag    1740
ccgctgcacc gtttcgagcg cttgcttgcc gccaccgttg ctggcgatag ccaccacttg    1800
gtccggggtc aggccatggt cctggcacag caccggcaac agccgctgca ccgtttcgag    1860
cgcttgcttg ccgccatcgt ggctggcgat agccaccact ggtccggag tcaggccatg    1920 gtcctggcac agcaccggca acagccgctg caccgtttcg agcgcttgct tgccgccatc    1980
gtggctggcg atagccacca cttggtccgg agtcaggcca tggtcctggc acagcaccgg    2040
caacagccgc tgcaccgttt cgagcgcttg cttgccgcca ccgttgctgg cgatagccac    2100
cacttggtcc ggggtcaggc catggtcctg gcacagcacc ggcaacagcc gctgcaccgt    2160
ttcgagcgct tgcttgccgc caccgttgct ggcgatagcc accacttggt ccggggtcag    2220
gccatggtcc tggcacagca ccggcaacag ccgctgcacc gtttcgagcg cttgcttgcc    2280
gccatcgtgg ctggcgatag ccaccacttg gtccggagtc aggccatggt cctggcacag    2340
caccggcaac agccgctgca ccgtttcgag cgcttgcttg ccgccaatgt tgctggcgat    2400
agccaccact ggtccggggg tcaggccatg gtcctggcac agcaccggca acagccgctg    2460
caccgtttcg agcgcttgct tgccgccatc gtggctggcg atagccacca cttggtccgg    2520
agtcaggcca tggtcctggc acagcaccgg caacagccgc tgcaccgttt cgagcgcttg    2580
cttgccgcca ccgttgctgg cgatagccac cacttggtcc ggggtcaggc catggtcctg    2640
gcacagcacc ggcaacagcc gctgcaccgt ttcgagcgct tgcttgccgc caccgttgct    2700
ggcgatagcc accacttggt ccggggtcag gccatggtcc tggcacagca ccggcaacag    2760
ccgctgcacc gtttcgagcg cttgcttgcc gccatcgtgg ctggcgatag ccaccacttg    2820
gtccggggtc aggttcaggg gggcacccgt cagtgcattg cgcgatgcat gcactgcctc    2880
cattgcggtc acgccgccac gttttgcaat cttcacaagt tggcctgtgt ccaactgtaa    2940
cggcggacct ctcaactccc ccgcatccgt gagcaaggcc tccagggcgc gtgcgccgga    3000
ccactgtttg ccgacgccaa cgatgtcttc gtgtgtcgcc tctggcaacg ccgtgattat    3060
gtgctgatac gtgacagcga cggtccctaa cgctgccggg tgttggctga gcgcaacgat    3120
gtgcgcgtgt gtaaacccat ggcccaccag tgcctcgtgg tgctgcgcca ctgtcgaacg    3180
caccttcggt ttgatcttct cttgctgctg ctgactgtag ccgagcgtgc gtagatccac    3240
ctgcgcggcc ggcgaagcgt cggagggttg cgcagcacgc cgtcgcgggg ccggcttggc    3300
gcgcggcggc cgcgcggcag tgacagcgac acgcacggtg ggtggcgggt catcggctgc    3360
acgcagagcc gattgcgcct catcccactc tgctggggca gccgctgtat gcggcgtgcc    3420
gacggcaggc atcgaatcaa gaagcgatgt atcaagaagc gacggatcga acggacggag    3480
cagatcgctg aagctgcccg ccgagaacgc aggtgagggc caggggggag atggcagccg    3540
ggtccgggac accgtccgcc gagcgggcaa gccatccaga gggctgccag caggcgcaga    3600 cacccccacga tctgcagtcg gctgaaccct atccggttgg ggtccgggca gaagctcgcg    3660
ggcaggactt ggcctgcgcg gacgaatggg atccat                              3696
```

<210> SEQ ID NO 5
<211> LENGTH: 1232

<212> TYPE: PRT
<213> ORGANISM: Artificial Sequence
<220> FEATURE:
<223> OTHER INFORMATION: pTAL1180 translated 3'-5'

<400> SEQUENCE: 5

Met Asp Pro Ile Arg Pro Arg Arg Pro Ser Pro Ala Arg Glu Leu Leu
1               5                   10                  15

Pro Gly Pro Gln Pro Asp Arg Val Gln Pro Thr Ala Asp Arg Gly Val
            20                  25                  30

Ser Ala Pro Ala Gly Ser Pro Leu Asp Gly Leu Pro Ala Arg Arg Thr
        35                  40                  45

Val Ser Arg Thr Arg Leu Pro Ser Pro Ala Pro Ser Pro Ala Phe
    50                  55                  60

Ser Ala Gly Ser Phe Ser Asp Leu Leu Arg Pro Phe Asp Pro Ser Leu
65              70                  75                  80

Leu Asp Thr Ser Leu Leu Asp Ser Met Pro Ala Val Gly Thr Pro His
                85                  90                  95

Thr Ala Ala Ala Pro Ala Glu Trp Asp Glu Ala Gln Ser Ala Leu Arg
            100                 105                 110

Ala Ala Asp Asp Pro Pro Pro Thr Val Arg Val Ala Val Thr Ala Ala
        115                 120                 125

Arg Pro Pro Arg Ala Lys Pro Ala Pro Arg Arg Ala Ala Gln Pro
130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Thr Tyr Gln His Ile Ile Thr Ala Leu Pro Glu Ala Thr His Glu Asp
210                 215                 220

Ile Val Gly Val Gly Lys Gln Trp Ser Gly Ala Arg Ala Leu Glu Ala
225                 230                 235                 240

Leu Leu Thr Asp Ala Gly Glu Leu Arg Gly Pro Pro Leu Gln Leu Asp
                245                 250                 255

Thr Gly Gln Leu Val Lys Ile Ala Lys Arg Gly Gly Val Thr Ala Met
            260                 265                 270

Glu Ala Val His Ala Ser Arg Asn Ala Leu Thr Gly Ala Pro Leu Asn
        275                 280                 285

Leu Thr Pro Asp Gln Val Val Ala Ile Ala Ser His Asp Gly Gly Lys
290                 295                 300

Gln Ala Leu Glu Thr Val Gln Arg Leu Leu Pro Val Leu Cys Gln Asp
305                 310                 315                 320

His Gly Leu Thr Pro Asp Gln Val Val Ala Ile Ala Ser His Asp Gly
                325                 330                 335

Gly Lys Gln Ala Leu Glu Thr Val Gln Arg Leu Leu Pro Val Leu Cys
            340                 345                 350

Gln Asp His Gly Leu Thr Pro Asp Gln Val Val Ala Ile Ala Ser His
        355                 360                 365

Asp Gly Gly Lys Gln Ala Leu Glu Thr Val Gln Arg Leu Leu Pro Val
370                 375                 380

```
Leu Cys Gln Asp His Gly Leu Thr Pro Asp Gln Val Val Ala Ile Ala
385                 390                 395                 400

Ser His Asp Gly Gly Lys Gln Ala Leu Glu Thr Val Gln Arg Leu Leu
            405                 410                 415

Pro Val Leu Cys Gln Asp His Gly Leu Thr Pro Asp Gln Val Val Ala
                420                 425                 430

Ile Ala Ser Asn Gly Gly Lys Gln Ala Leu Glu Thr Val Gln Arg
        435                 440                 445

Leu Leu Pro Val Leu Cys Gln Asp His Gly Leu Thr Pro Asp Gln Val
    450                 455                 460

Val Ala Ile Ala Ser Asn Gly Gly Lys Gln Ala Leu Glu Thr Val
465                 470                 475                 480

Gln Arg Leu Leu Pro Val Leu Cys Gln Asp His Gly Leu Thr Pro Asp
                485                 490                 495

Gln Val Val Ala Ile Ala Ser Asn Ile Gly Gly Lys Gln Ala Leu Glu
                500                 505                 510

Thr Val Gln Arg Leu Leu Pro Val Leu Cys Gln Asp His Gly Leu Thr
        515                 520                 525

Pro Asp Gln Val Val Ala Ile Ala Ser Asn Gly Gly Gly Lys Gln Ala
    530                 535                 540

Leu Glu Thr Val Gln Arg Leu Leu Pro Val Leu Cys Gln Asp His Gly
545                 550                 555                 560

Leu Thr Pro Asp Gln Val Val Ala Ile Ala Ser Asn Ile Gly Gly Lys
                565                 570                 575

Gln Ala Leu Glu Thr Val Gln Arg Leu Leu Pro Val Leu Cys Gln Asp
                580                 585                 590

His Gly Leu Thr Pro Asp Gln Val Val Ala Ile Ala Ser Asn Gly Gly
        595                 600                 605

Gly Lys Gln Ala Leu Glu Thr Val Gln Arg Leu Leu Pro Val Leu Cys
    610                 615                 620

Gln Asp His Gly Leu Thr Pro Asp Gln Val Val Ala Ile Ala Ser Asn
625                 630                 635                 640

Ile Gly Gly Lys Gln Ala Leu Glu Thr Val Gln Arg Leu Leu Pro Val
                645                 650                 655

Leu Cys Gln Asp His Gly Leu Thr Pro Asp Gln Val Val Ala Ile Ala
                660                 665                 670

Ser Asn Gly Gly Gly Lys Gln Ala Leu Glu Thr Val Gln Arg Leu Leu
        675                 680                 685

Pro Val Leu Cys Gln Asp His Gly Leu Thr Pro Asp Gln Val Val Ala
    690                 695                 700

Ile Ala Ser His Asp Gly Gly Lys Gln Ala Leu Glu Thr Val Gln Arg
705                 710                 715                 720

Leu Leu Pro Val Leu Cys Gln Asp His Gly Leu Thr Pro Asp Gln Val
                725                 730                 735

Val Ala Ile Ala Ser Asn Ile Gly Gly Lys Gln Ala Leu Glu Thr Val
                740                 745                 750

Gln Arg Leu Leu Pro Val Leu Cys Gln Asp His Gly Leu Thr Pro Asp
        755                 760                 765

Gln Val Val Ala Ile Ala Ser His Asp Gly Gly Lys Gln Ala Leu Glu
    770                 775                 780

Thr Val Gln Arg Leu Leu Pro Val Leu Cys Gln Asp His Gly Leu Thr
785                 790                 795                 800

Pro Asp Gln Val Val Ala Ile Ala Ser Asn Ile Gly Gly Lys Gln Ala
```

```
                805                 810                 815
Leu Glu Thr Val Gln Arg Leu Leu Pro Val Leu Cys Gln Asp His Gly
            820                 825                 830
Leu Thr Pro Asp Gln Val Val Ala Ile Ala Ser Asn Ile Gly Gly Lys
            835                 840                 845
Gln Ala Leu Glu Thr Val Gln Arg Leu Leu Pro Val Leu Cys Gln Asp
            850                 855                 860
His Gly Leu Thr Pro Asp Gln Val Val Ala Ile Ala Ser His Asp Gly
865                 870                 875                 880
Gly Lys Gln Ala Leu Glu Thr Val Gln Arg Leu Leu Pro Val Leu Cys
                885                 890                 895
Gln Asp His Gly Leu Thr Pro Asp Gln Val Val Ala Ile Ala Ser His
            900                 905                 910
Asp Gly Gly Lys Gln Ala Leu Glu Thr Val Gln Arg Leu Leu Pro Val
            915                 920                 925
Leu Cys Gln Asp His Gly Leu Thr Pro Asp Gln Val Val Ala Ile Ala
            930                 935                 940
Ser Asn Ile Gly Gly Lys Gln Ala Leu Glu Ser Ile Val Ala Gln Leu
945                 950                 955                 960
Ser Arg Pro Asp Pro Ala Leu Ala Ala Leu Thr Asn Asp His Leu Val
                965                 970                 975
Ala Leu Ala Cys Leu Gly Gly Arg Pro Ala Met Asp Ala Val Lys Lys
            980                 985                 990
Gly Leu Pro His Ala Pro Glu Leu Ile Arg Arg Val Asn Arg Arg Ile
            995                1000                1005
Gly Glu Arg Thr Ser His Arg Val Ala Asp Tyr Ala Gln Val Val
           1010                1015                1020
Arg Val Leu Glu Phe Phe Gln Cys His Ser His Pro Ala Tyr Ala
           1025                1030                1035
Phe Asp Glu Ala Met Thr Gln Phe Gly Met Ser Arg Asn Gly Leu
           1040                1045                1050
Val Gln Leu Phe Arg Arg Val Gly Val Thr Glu Leu Glu Ala Arg
           1055                1060                1065
Gly Gly Thr Leu Pro Pro Ala Ser Gln Arg Trp Asp Arg Ile Leu
           1070                1075                1080
Gln Ala Ser Gly Met Lys Arg Ala Lys Pro Ser Pro Thr Ser Ala
           1085                1090                1095
Gln Thr Pro Asp Gln Ala Ser Leu His Ala Phe Ala Asp Ser Leu
           1100                1105                1110
Glu Arg Asp Leu Asp Ala Pro Ser Pro Met His Glu Gly Asp Gln
           1115                1120                1125
Thr Arg Ala Ser Ser Arg Lys Arg Ser Arg Ser Asp Arg Ala Val
           1130                1135                1140
Thr Gly Pro Ser Ala Gln Gln Ala Val Glu Val Arg Val Pro Glu
           1145                1150                1155
Gln Arg Asp Ala Leu His Leu Pro Leu Ser Trp Arg Val Lys Arg
           1160                1165                1170
Pro Arg Thr Arg Ile Trp Gly Gly Leu Pro Asp Pro Gly Thr Pro
           1175                1180                1185
Met Ala Ala Asp Leu Ala Ala Ser Ser Thr Val Met Trp Glu Gln
           1190                1195                1200
Asp Ala Asp Pro Phe Ala Gly Ala Ala Asp Asp Phe Pro Ala Phe
           1205                1210                1215
```

Asn Glu Glu Glu Leu Ala Trp Leu Met Glu Leu Leu Pro Gln
    1220                1225                1230

<210> SEQ ID NO 6
<211> LENGTH: 1232
<212> TYPE: PRT
<213> ORGANISM: Artificial Sequence
<220> FEATURE:
<223> OTHER INFORMATION: pTAL1181 translated 3'-5'

<400> SEQUENCE: 6

Met Asp Pro Ile Arg Pro Arg Pro Ser Pro Ala Arg Glu Leu Leu
1               5                   10                  15

Pro Gly Pro Gln Pro Asp Arg Val Gln Pro Thr Ala Asp Arg Gly Val
            20                  25                  30

Ser Ala Pro Ala Gly Ser Pro Leu Asp Gly Leu Pro Ala Arg Arg Thr
                35                  40                  45

Val Ser Arg Thr Arg Leu Pro Ser Pro Ala Pro Ser Pro Ala Phe
50                  55                  60

Ser Ala Gly Ser Phe Ser Asp Leu Leu Arg Pro Phe Asp Pro Ser Leu
65                  70                  75                  80

Leu Asp Thr Ser Leu Leu Asp Ser Met Pro Ala Val Gly Thr Pro His
                85                  90                  95

Thr Ala Ala Ala Pro Ala Glu Trp Asp Glu Ala Gln Ser Ala Leu Arg
            100                 105                 110

Ala Ala Asp Asp Pro Pro Pro Thr Val Arg Val Ala Val Thr Ala Ala
            115                 120                 125

Arg Pro Pro Arg Ala Lys Pro Ala Pro Arg Arg Arg Ala Ala Gln Pro
        130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Thr Tyr Gln His Ile Ile Thr Ala Leu Pro Glu Ala Thr His Glu Asp
    210                 215                 220

Ile Val Gly Val Gly Lys Gln Trp Ser Gly Ala Arg Ala Leu Glu Ala
225                 230                 235                 240

Leu Leu Thr Asp Ala Gly Glu Leu Arg Gly Pro Pro Leu Gln Leu Asp
                245                 250                 255

Thr Gly Gln Leu Val Lys Ile Ala Lys Arg Gly Gly Val Thr Ala Met
            260                 265                 270

Glu Ala Val His Ala Ser Arg Asn Ala Leu Thr Gly Ala Pro Leu Asn
        275                 280                 285

Leu Thr Pro Asp Gln Val Val Ala Ile Ala Ser His Asp Gly Gly Lys
    290                 295                 300

Gln Ala Leu Glu Thr Val Gln Arg Leu Leu Pro Val Leu Cys Gln Asp
305                 310                 315                 320

His Gly Leu Thr Pro Asp Gln Val Val Ala Ile Ala Ser His Asp Gly
                325                 330                 335

Gly Lys Gln Ala Leu Glu Thr Val Gln Arg Leu Leu Pro Val Leu Cys
            340                 345                 350

```
Gln Asp His Gly Leu Thr Pro Asp Gln Val Val Ala Ile Ala Ser Asn
        355                 360                 365

Ile Gly Gly Lys Gln Ala Leu Glu Thr Val Gln Arg Leu Leu Pro Val
        370                 375                 380

Leu Cys Gln Asp His Gly Leu Thr Pro Asp Gln Val Val Ala Ile Ala
385                 390                 395                 400

Ser Asn Ile Gly Gly Lys Gln Ala Leu Glu Thr Val Gln Arg Leu Leu
                405                 410                 415

Pro Val Leu Cys Gln Asp His Gly Leu Thr Pro Asp Gln Val Val Ala
            420                 425                 430

Ile Ala Ser Asn Gly Gly Lys Gln Ala Leu Glu Thr Val Gln Arg
        435                 440                 445

Leu Leu Pro Val Leu Cys Gln Asp His Gly Leu Thr Pro Asp Gln Val
        450                 455                 460

Val Ala Ile Ala Ser His Asp Gly Gly Lys Gln Ala Leu Glu Thr Val
465                 470                 475                 480

Gln Arg Leu Leu Pro Val Leu Cys Gln Asp His Gly Leu Thr Pro Asp
                485                 490                 495

Gln Val Val Ala Ile Ala Ser Asn Ile Gly Gly Lys Gln Ala Leu Glu
            500                 505                 510

Thr Val Gln Arg Leu Leu Pro Val Leu Cys Gln Asp His Gly Leu Thr
        515                 520                 525

Pro Asp Gln Val Val Ala Ile Ala Ser His Asp Gly Gly Lys Gln Ala
        530                 535                 540

Leu Glu Thr Val Gln Arg Leu Leu Pro Val Leu Cys Gln Asp His Gly
545                 550                 555                 560

Leu Thr Pro Asp Gln Val Val Ala Ile Ala Ser Asn Ile Gly Gly Lys
                565                 570                 575

Gln Ala Leu Glu Thr Val Gln Arg Leu Leu Pro Val Leu Cys Gln Asp
            580                 585                 590

His Gly Leu Thr Pro Asp Gln Val Val Ala Ile Ala Ser Asn Gly Gly
        595                 600                 605

Gly Lys Gln Ala Leu Glu Thr Val Gln Arg Leu Leu Pro Val Leu Cys
        610                 615                 620

Gln Asp His Gly Leu Thr Pro Asp Gln Val Val Ala Ile Ala Ser Asn
625                 630                 635                 640

Gly Gly Gly Lys Gln Ala Leu Glu Thr Val Gln Arg Leu Leu Pro Val
                645                 650                 655

Leu Cys Gln Asp His Gly Leu Thr Pro Asp Gln Val Val Ala Ile Ala
            660                 665                 670

Ser His Asp Gly Gly Lys Gln Ala Leu Glu Thr Val Gln Arg Leu Leu
        675                 680                 685

Pro Val Leu Cys Gln Asp His Gly Leu Thr Pro Asp Gln Val Val Ala
        690                 695                 700

Ile Ala Ser Asn Ile Gly Gly Lys Gln Ala Leu Glu Thr Val Gln Arg
705                 710                 715                 720

Leu Leu Pro Val Leu Cys Gln Asp His Gly Leu Thr Pro Asp Gln Val
                725                 730                 735

Val Ala Ile Ala Ser Asn Ile Gly Gly Lys Gln Ala Leu Glu Thr Val
            740                 745                 750

Gln Arg Leu Leu Pro Val Leu Cys Gln Asp His Gly Leu Thr Pro Asp
        755                 760                 765
```

```
Gln Val Val Ala Ile Ala Ser His Asp Gly Gly Lys Gln Ala Leu Glu
    770                 775                 780

Thr Val Gln Arg Leu Leu Pro Val Leu Cys Gln Asp His Gly Leu Thr
785                 790                 795                 800

Pro Asp Gln Val Val Ala Ile Ala Ser His Asp Gly Gly Lys Gln Ala
                805                 810                 815

Leu Glu Thr Val Gln Arg Leu Leu Pro Val Leu Cys Gln Asp His Gly
        820                 825                 830

Leu Thr Pro Asp Gln Val Val Ala Ile Ala Ser Asn Ile Gly Gly Lys
            835                 840                 845

Gln Ala Leu Glu Thr Val Gln Arg Leu Leu Pro Val Leu Cys Gln Asp
850                 855                 860

His Gly Leu Thr Pro Asp Gln Val Val Ala Ile Ala Ser Asn Ile Gly
865                 870                 875                 880

Gly Lys Gln Ala Leu Glu Thr Val Gln Arg Leu Leu Pro Val Leu Cys
                885                 890                 895

Gln Asp His Gly Leu Thr Pro Asp Gln Val Val Ala Ile Ala Ser Asn
        900                 905                 910

His Gly Gly Lys Gln Ala Leu Glu Thr Val Gln Arg Leu Leu Pro Val
            915                 920                 925

Leu Cys Gln Asp His Gly Leu Thr Pro Asp Gln Val Val Ala Ile Ala
930                 935                 940

Ser Asn Gly Gly Gly Lys Gln Ala Leu Glu Ser Ile Val Ala Gln Leu
945                 950                 955                 960

Ser Arg Pro Asp Pro Ala Leu Ala Ala Leu Thr Asn Asp His Leu Val
                965                 970                 975

Ala Leu Ala Cys Leu Gly Gly Arg Pro Ala Met Asp Ala Val Lys Lys
        980                 985                 990

Gly Leu Pro His Ala Pro Glu Leu  Ile Arg Arg Val Asn  Arg Arg Ile
            995                 1000                 1005

Gly Glu  Arg Thr Ser His Arg  Val Ala Asp Tyr Ala  Gln Val Val
    1010                 1015                 1020

Arg Val  Leu Glu Phe Phe Gln  Cys His Ser His Pro  Ala Tyr Ala
    1025                 1030                 1035

Phe Asp  Glu Ala Met Thr Gln  Phe Gly Met Ser Arg  Asn Gly Leu
    1040                 1045                 1050

Val Gln  Leu Phe Arg Arg Val  Gly Val Thr Glu Leu  Glu Ala Arg
    1055                 1060                 1065

Gly Gly  Thr Leu Pro Pro Ala  Ser Gln Arg Trp Asp  Arg Ile Leu
    1070                 1075                 1080

Gln Ala  Ser Gly Met Lys Arg  Ala Lys Pro Ser Pro  Thr Ser Ala
    1085                 1090                 1095

Gln Thr  Pro Asp Gln Ala Ser  Leu His Ala Phe Ala  Asp Ser Leu
    1100                 1105                 1110

Glu Arg  Asp Leu Asp Ala Pro  Ser Pro Met His Glu  Gly Asp Gln
    1115                 1120                 1125

Thr Arg  Ala Ser Ser Arg Lys  Arg Ser Arg Ser Asp  Arg Ala Val
    1130                 1135                 1140

Thr Gly  Pro Ser Ala Gln Gln  Ala Val Glu Val Arg  Val Pro Glu
    1145                 1150                 1155

Gln Arg  Asp Ala Leu His Leu  Pro Leu Ser Trp Arg  Val Lys Arg
    1160                 1165                 1170

Pro Arg  Thr Arg Ile Trp Gly  Gly Leu Pro Asp Pro  Gly Thr Pro
```

```
                1175                1180                1185
Met Ala Ala Asp Leu Ala Ala Ser Ser Thr Val Met Trp Glu Gln
            1190                1195                1200

Asp Ala Asp Pro Phe Ala Gly Ala Ala Asp Asp Phe Pro Ala Phe
            1205                1210                1215

Asn Glu Glu Glu Leu Ala Trp Leu Met Glu Leu Leu Pro Gln
            1220                1225                1230

<210> SEQ ID NO 7
<211> LENGTH: 1232
<212> TYPE: PRT
<213> ORGANISM: Artificial Sequence
<220> FEATURE:
<223> OTHER INFORMATION: pTAL1182 translated 3'-5'

<400> SEQUENCE: 7

Met Asp Pro Ile Arg Pro Arg Arg Pro Ser Pro Ala Arg Glu Leu Leu
1               5                   10                  15

Pro Gly Pro Gln Pro Asp Arg Val Gln Pro Thr Ala Asp Arg Gly Val
            20                  25                  30

Ser Ala Pro Ala Gly Ser Pro Leu Asp Gly Leu Pro Ala Arg Arg Thr
        35                  40                  45

Val Ser Arg Thr Arg Leu Pro Ser Pro Ala Pro Ser Pro Ala Phe
    50                  55                  60

Ser Ala Gly Ser Phe Ser Asp Leu Leu Arg Pro Phe Asp Pro Ser Leu
65                  70                  75                  80

Leu Asp Thr Ser Leu Leu Asp Ser Met Pro Ala Val Gly Thr Pro His
                85                  90                  95

Thr Ala Ala Ala Pro Ala Glu Trp Asp Glu Ala Gln Ser Ala Leu Arg
            100                 105                 110

Ala Ala Asp Asp Pro Pro Pro Thr Val Arg Val Ala Val Thr Ala Ala
        115                 120                 125

Arg Pro Pro Arg Ala Lys Pro Ala Pro Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Thr Tyr Gln His Ile Ile Thr Ala Leu Pro Glu Ala Thr His Glu Asp
    210                 215                 220

Ile Val Gly Val Gly Lys Gln Trp Ser Gly Ala Arg Ala Leu Glu Ala
225                 230                 235                 240

Leu Leu Thr Asp Ala Gly Glu Leu Arg Gly Pro Pro Leu Gln Leu Asp
                245                 250                 255

Thr Gly Gln Leu Val Lys Ile Ala Lys Arg Gly Gly Val Thr Ala Met
            260                 265                 270

Glu Ala Val His Ala Ser Arg Asn Ala Leu Thr Gly Ala Pro Leu Asn
        275                 280                 285

Leu Thr Pro Asp Gln Val Val Ala Ile Ala Ser Asn His Gly Gly Lys
    290                 295                 300

Gln Ala Leu Glu Thr Val Gln Arg Leu Leu Pro Val Leu Cys Gln Asp
```

```
            305                 310                 315                 320
His Gly Leu Thr Pro Asp Gln Val Val Ala Ile Ala Ser His Asp Gly
                325                 330                 335

Gly Lys Gln Ala Leu Glu Thr Val Gln Arg Leu Leu Pro Val Leu Cys
                340                 345                 350

Gln Asp His Gly Leu Thr Pro Asp Gln Val Val Ala Ile Ala Ser His
                355                 360                 365

Asp Gly Gly Lys Gln Ala Leu Glu Thr Val Gln Arg Leu Leu Pro Val
370                 375                 380

Leu Cys Gln Asp His Gly Leu Thr Pro Asp Gln Val Val Ala Ile Ala
385                 390                 395                 400

Ser His Asp Gly Gly Lys Gln Ala Leu Glu Thr Val Gln Arg Leu Leu
                405                 410                 415

Pro Val Leu Cys Gln Asp His Gly Leu Thr Pro Asp Gln Val Val Ala
                420                 425                 430

Ile Ala Ser Asn Ile Gly Gly Lys Gln Ala Leu Glu Thr Val Gln Arg
                435                 440                 445

Leu Leu Pro Val Leu Cys Gln Asp His Gly Leu Thr Pro Asp Gln Val
                450                 455                 460

Val Ala Ile Ala Ser Asn Gly Gly Lys Gln Ala Leu Glu Thr Val
465                 470                 475                 480

Gln Arg Leu Leu Pro Val Leu Cys Gln Asp His Gly Leu Thr Pro Asp
                485                 490                 495

Gln Val Val Ala Ile Ala Ser Asn His Gly Gly Lys Gln Ala Leu Glu
                500                 505                 510

Thr Val Gln Arg Leu Leu Pro Val Leu Cys Gln Asp His Gly Leu Thr
                515                 520                 525

Pro Asp Gln Val Val Ala Ile Ala Ser Asn Gly Gly Lys Gln Ala
                530                 535                 540

Leu Glu Thr Val Gln Arg Leu Leu Pro Val Leu Cys Gln Asp His Gly
545                 550                 555                 560

Leu Thr Pro Asp Gln Val Val Ala Ile Ala Ser Asn Ile Gly Gly Lys
                565                 570                 575

Gln Ala Leu Glu Thr Val Gln Arg Leu Leu Pro Val Leu Cys Gln Asp
                580                 585                 590

His Gly Leu Thr Pro Asp Gln Val Val Ala Ile Ala Ser His Asp Gly
                595                 600                 605

Gly Lys Gln Ala Leu Glu Thr Val Gln Arg Leu Leu Pro Val Leu Cys
                610                 615                 620

Gln Asp His Gly Leu Thr Pro Asp Gln Val Val Ala Ile Ala Ser Asn
625                 630                 635                 640

Ile Gly Gly Lys Gln Ala Leu Glu Thr Val Gln Arg Leu Leu Pro Val
                645                 650                 655

Leu Cys Gln Asp His Gly Leu Thr Pro Asp Gln Val Val Ala Ile Ala
                660                 665                 670

Ser His Asp Gly Gly Lys Gln Ala Leu Glu Thr Val Gln Arg Leu Leu
                675                 680                 685

Pro Val Leu Cys Gln Asp His Gly Leu Thr Pro Asp Gln Val Val Ala
                690                 695                 700

Ile Ala Ser Asn Gly Gly Gly Lys Gln Ala Leu Glu Thr Val Gln Arg
705                 710                 715                 720

Leu Leu Pro Val Leu Cys Gln Asp His Gly Leu Thr Pro Asp Gln Val
                725                 730                 735
```

```
Val Ala Ile Ala Ser His Asp Gly Gly Lys Gln Ala Leu Glu Thr Val
                740                 745                 750

Gln Arg Leu Leu Pro Val Leu Cys Gln Asp His Gly Leu Thr Pro Asp
            755                 760                 765

Gln Val Val Ala Ile Ala Ser His Asp Gly Gly Lys Gln Ala Leu Glu
    770                 775                 780

Thr Val Gln Arg Leu Leu Pro Val Leu Cys Gln Asp His Gly Leu Thr
785                 790                 795                 800

Pro Asp Gln Val Val Ala Ile Ala Ser Asn Ile Gly Gly Lys Gln Ala
                805                 810                 815

Leu Glu Thr Val Gln Arg Leu Leu Pro Val Leu Cys Gln Asp His Gly
            820                 825                 830

Leu Thr Pro Asp Gln Val Val Ala Ile Ala Ser Asn Gly Gly Gly Lys
        835                 840                 845

Gln Ala Leu Glu Thr Val Gln Arg Leu Leu Pro Val Leu Cys Gln Asp
    850                 855                 860

His Gly Leu Thr Pro Asp Gln Val Val Ala Ile Ala Ser His Asp Gly
865                 870                 875                 880

Gly Lys Gln Ala Leu Glu Thr Val Gln Arg Leu Leu Pro Val Leu Cys
                885                 890                 895

Gln Asp His Gly Leu Thr Pro Asp Gln Val Val Ala Ile Ala Ser Asn
            900                 905                 910

Ile Gly Gly Lys Gln Ala Leu Glu Thr Val Gln Arg Leu Leu Pro Val
        915                 920                 925

Leu Cys Gln Asp His Gly Leu Thr Pro Asp Gln Val Val Ala Ile Ala
    930                 935                 940

Ser His Asp Gly Gly Lys Gln Ala Leu Glu Ser Ile Val Ala Gln Leu
945                 950                 955                 960

Ser Arg Pro Asp Pro Ala Leu Ala Ala Leu Thr Asn Asp His Leu Val
                965                 970                 975

Ala Leu Ala Cys Leu Gly Gly Arg Pro Ala Met Asp Ala Val Lys Lys
            980                 985                 990

Gly Leu Pro His Ala Pro Glu Leu Ile Arg Arg Val Asn Arg Arg Ile
        995                 1000                1005

Gly Glu Arg Thr Ser His Arg Val Ala Asp Tyr Ala Gln Val Val
        1010                1015                1020

Arg Val Leu Glu Phe Phe Gln Cys His Ser His Pro Ala Tyr Ala
    1025                1030                1035

Phe Asp Glu Ala Met Thr Gln Phe Gly Met Ser Arg Asn Gly Leu
    1040                1045                1050

Val Gln Leu Phe Arg Arg Val Gly Val Thr Glu Leu Glu Ala Arg
    1055                1060                1065

Gly Gly Thr Leu Pro Pro Ala Ser Gln Arg Trp Asp Arg Ile Leu
    1070                1075                1080

Gln Ala Ser Gly Met Lys Arg Ala Lys Pro Ser Pro Thr Ser Ala
    1085                1090                1095

Gln Thr Pro Asp Gln Ala Ser Leu His Ala Phe Ala Asp Ser Leu
    1100                1105                1110

Glu Arg Asp Leu Asp Ala Pro Ser Pro Met His Glu Gly Asp Gln
    1115                1120                1125

Thr Arg Ala Ser Ser Arg Lys Arg Ser Arg Ser Asp Arg Ala Val
    1130                1135                1140
```

```
Thr Gly Pro Ser Ala Gln Gln Ala Val Glu Val Arg Val Pro Glu
    1145                1150                1155

Gln Arg Asp Ala Leu His Leu Pro Leu Ser Trp Arg Val Lys Arg
    1160                1165                1170

Pro Arg Thr Arg Ile Trp Gly Gly Leu Pro Asp Pro Gly Thr Pro
    1175                1180                1185

Met Ala Ala Asp Leu Ala Ala Ser Ser Thr Val Met Trp Glu Gln
    1190                1195                1200

Asp Ala Asp Pro Phe Ala Gly Ala Ala Asp Phe Pro Ala Phe
    1205                1210                1215

Asn Glu Glu Glu Leu Ala Trp Leu Met Glu Leu Leu Pro Gln
    1220                1225                1230

<210> SEQ ID NO 8
<211> LENGTH: 1232
<212> TYPE: PRT
<213> ORGANISM: Artificial Sequence
<220> FEATURE:
<223> OTHER INFORMATION: pTAL1183 translated 3'-5'

<400> SEQUENCE: 8

Met Asp Pro Ile Arg Pro Arg Arg Pro Ser Pro Ala Arg Glu Leu Leu
1               5                   10                  15

Pro Gly Pro Gln Pro Asp Arg Val Gln Pro Thr Ala Asp Arg Gly Val
            20                  25                  30

Ser Ala Pro Ala Gly Ser Pro Leu Asp Gly Leu Pro Ala Arg Arg Thr
        35                  40                  45

Val Ser Arg Thr Arg Leu Pro Ser Pro Ala Pro Ser Pro Ala Phe
50                  55                  60

Ser Ala Gly Ser Phe Ser Asp Leu Leu Arg Pro Phe Asp Pro Ser Leu
65                  70                  75                  80

Leu Asp Thr Ser Leu Leu Asp Ser Met Pro Ala Val Gly Thr Pro His
                85                  90                  95

Thr Ala Ala Ala Pro Ala Glu Trp Asp Glu Ala Gln Ser Ala Leu Arg
            100                 105                 110

Ala Ala Asp Asp Pro Pro Pro Thr Val Arg Val Ala Val Thr Ala Ala
        115                 120                 125

Arg Pro Pro Arg Ala Lys Pro Ala Pro Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Thr Tyr Gln His Ile Ile Thr Ala Leu Pro Glu Ala Thr His Glu Asp
    210                 215                 220

Ile Val Gly Val Gly Lys Gln Trp Ser Gly Ala Arg Ala Leu Glu Ala
225                 230                 235                 240

Leu Leu Thr Asp Ala Gly Glu Leu Arg Gly Pro Pro Leu Gln Leu Asp
                245                 250                 255

Thr Gly Gln Leu Val Lys Ile Ala Lys Arg Gly Gly Val Thr Ala Met
            260                 265                 270
```

```
Glu Ala Val His Ala Ser Arg Asn Ala Leu Thr Gly Ala Pro Leu Asn
            275                 280                 285

Leu Thr Pro Asp Gln Val Val Ala Ile Ala Ser His Asp Gly Gly Lys
        290                 295                 300

Gln Ala Leu Glu Thr Val Gln Arg Leu Leu Pro Val Leu Cys Gln Asp
305                 310                 315                 320

His Gly Leu Thr Pro Asp Gln Val Val Ala Ile Ala Ser Asn Gly Gly
                325                 330                 335

Gly Lys Gln Ala Leu Glu Thr Val Gln Arg Leu Leu Pro Val Leu Cys
            340                 345                 350

Gln Asp His Gly Leu Thr Pro Asp Gln Val Val Ala Ile Ala Ser Asn
        355                 360                 365

Gly Gly Gly Lys Gln Ala Leu Glu Thr Val Gln Arg Leu Leu Pro Val
    370                 375                 380

Leu Cys Gln Asp His Gly Leu Thr Pro Asp Gln Val Val Ala Ile Ala
385                 390                 395                 400

Ser His Asp Gly Gly Lys Gln Ala Leu Glu Thr Val Gln Arg Leu Leu
                405                 410                 415

Pro Val Leu Cys Gln Asp His Gly Leu Thr Pro Asp Gln Val Val Ala
            420                 425                 430

Ile Ala Ser Asn Ile Gly Gly Lys Gln Ala Leu Glu Thr Val Gln Arg
        435                 440                 445

Leu Leu Pro Val Leu Cys Gln Asp His Gly Leu Thr Pro Asp Gln Val
    450                 455                 460

Val Ala Ile Ala Ser His Asp Gly Gly Lys Gln Ala Leu Glu Thr Val
465                 470                 475                 480

Gln Arg Leu Leu Pro Val Leu Cys Gln Asp His Gly Leu Thr Pro Asp
                485                 490                 495

Gln Val Val Ala Ile Ala Ser Asn Gly Gly Gly Lys Gln Ala Leu Glu
            500                 505                 510

Thr Val Gln Arg Leu Leu Pro Val Leu Cys Gln Asp His Gly Leu Thr
        515                 520                 525

Pro Asp Gln Val Val Ala Ile Ala Ser Asn Gly Gly Gly Lys Gln Ala
    530                 535                 540

Leu Glu Thr Val Gln Arg Leu Leu Pro Val Leu Cys Gln Asp His Gly
545                 550                 555                 560

Leu Thr Pro Asp Gln Val Val Ala Ile Ala Ser His Asp Gly Gly Lys
                565                 570                 575

Gln Ala Leu Glu Thr Val Gln Arg Leu Leu Pro Val Leu Cys Gln Asp
            580                 585                 590

His Gly Leu Thr Pro Asp Gln Val Val Ala Ile Ala Ser His Asp Gly
        595                 600                 605

Gly Lys Gln Ala Leu Glu Thr Val Gln Arg Leu Leu Pro Val Leu Cys
    610                 615                 620

Gln Asp His Gly Leu Thr Pro Asp Gln Val Val Ala Ile Ala Ser Asn
625                 630                 635                 640

Gly Gly Gly Lys Gln Ala Leu Glu Thr Val Gln Arg Leu Leu Pro Val
                645                 650                 655

Leu Cys Gln Asp His Gly Leu Thr Pro Asp Gln Val Val Ala Ile Ala
            660                 665                 670

Ser His Asp Gly Gly Lys Gln Ala Leu Glu Thr Val Gln Arg Leu Leu
        675                 680                 685

Pro Val Leu Cys Gln Asp His Gly Leu Thr Pro Asp Gln Val Val Ala
```

-continued

```
            690                 695                 700
Ile Ala Ser Asn His Gly Gly Lys Gln Ala Leu Glu Thr Val Gln Arg
705                 710                 715                 720

Leu Leu Pro Val Leu Cys Gln Asp His Gly Leu Thr Pro Asp Gln Val
                725                 730                 735

Val Ala Ile Ala Ser Asn Gly Gly Lys Gln Ala Leu Glu Thr Val
                740                 745                 750

Gln Arg Leu Leu Pro Val Leu Cys Gln Asp His Gly Leu Thr Pro Asp
            755                 760                 765

Gln Val Val Ala Ile Ala Ser His Asp Gly Gly Lys Gln Ala Leu Glu
        770                 775                 780

Thr Val Gln Arg Leu Leu Pro Val Leu Cys Gln Asp His Gly Leu Thr
785                 790                 795                 800

Pro Asp Gln Val Val Ala Ile Ala Ser His Asp Gly Gly Lys Gln Ala
                805                 810                 815

Leu Glu Thr Val Gln Arg Leu Leu Pro Val Leu Cys Gln Asp His Gly
                820                 825                 830

Leu Thr Pro Asp Gln Val Val Ala Ile Ala Ser Asn Gly Gly Gly Lys
            835                 840                 845

Gln Ala Leu Glu Thr Val Gln Arg Leu Leu Pro Val Leu Cys Gln Asp
        850                 855                 860

His Gly Leu Thr Pro Asp Gln Val Val Ala Ile Ala Ser His Asp Gly
865                 870                 875                 880

Gly Lys Gln Ala Leu Glu Thr Val Gln Arg Leu Leu Pro Val Leu Cys
                885                 890                 895

Gln Asp His Gly Leu Thr Pro Asp Gln Val Val Ala Ile Ala Ser Asn
                900                 905                 910

Ile Gly Gly Lys Gln Ala Leu Glu Thr Val Gln Arg Leu Leu Pro Val
            915                 920                 925

Leu Cys Gln Asp His Gly Leu Thr Pro Asp Gln Val Val Ala Ile Ala
        930                 935                 940

Ser Asn Gly Gly Gly Lys Gln Ala Leu Glu Ser Ile Val Ala Gln Leu
945                 950                 955                 960

Ser Arg Pro Asp Pro Ala Leu Ala Ala Leu Thr Asn Asp His Leu Val
                965                 970                 975

Ala Leu Ala Cys Leu Gly Gly Arg Pro Ala Met Asp Ala Val Lys Lys
                980                 985                 990

Gly Leu Pro His Ala Pro Glu Leu Ile Arg Arg Val Asn Arg Arg Ile
            995                 1000                1005

Gly Glu Arg Thr Ser His Arg Val Ala Asp Tyr Ala Gln Val Val
        1010                1015                1020

Arg Val Leu Glu Phe Phe Gln Cys His Ser His Pro Ala Tyr Ala
    1025                1030                1035

Phe Asp Glu Ala Met Thr Gln Phe Gly Met Ser Arg Asn Gly Leu
    1040                1045                1050

Val Gln Leu Phe Arg Arg Val Gly Val Thr Glu Leu Glu Ala Arg
    1055                1060                1065

Gly Gly Thr Leu Pro Pro Ala Ser Gln Arg Trp Asp Arg Ile Leu
    1070                1075                1080

Gln Ala Ser Gly Met Lys Arg Ala Lys Pro Ser Pro Thr Ser Ala
    1085                1090                1095

Gln Thr Pro Asp Gln Ala Ser Leu His Ala Phe Ala Asp Ser Leu
    1100                1105                1110
```

```
Glu Arg Asp Leu Asp Ala Pro Ser Pro Met His Glu Gly Asp Gln
    1115                1120                1125

Thr Arg Ala Ser Ser Arg Lys Arg Ser Arg Ser Asp Arg Ala Val
    1130                1135                1140

Thr Gly Pro Ser Ala Gln Gln Ala Val Glu Val Arg Val Pro Glu
    1145                1150                1155

Gln Arg Asp Ala Leu His Leu Pro Leu Ser Trp Arg Val Lys Arg
    1160                1165                1170

Pro Arg Thr Arg Ile Trp Gly Gly Leu Pro Asp Pro Gly Thr Pro
    1175                1180                1185

Met Ala Ala Asp Leu Ala Ala Ser Ser Thr Val Met Trp Glu Gln
    1190                1195                1200

Asp Ala Asp Pro Phe Ala Gly Ala Ala Asp Asp Phe Pro Ala Phe
    1205                1210                1215

Asn Glu Glu Glu Leu Ala Trp Leu Met Glu Leu Leu Pro Gln
    1220                1225                1230

<210> SEQ ID NO 9
<211> LENGTH: 34
<212> TYPE: PRT
<213> ORGANISM: Artificial Sequence
<220> FEATURE:
<223> OTHER INFORMATION: Repeat domain

<400> SEQUENCE: 9

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
                20                  25                  30

His Gly

<210> SEQ ID NO 10
<211> LENGTH: 2930
<212> TYPE: DNA
<213> ORGANISM: Glycine max
<220> FEATURE:
<221> NAME/KEY: misc_feature
<222> LOCATION: (1)..(882)
<223> OTHER INFORMATION: promoter and 5' UTR region

<400> SEQUENCE: 10
cccttcatag aggacaacct tcatgtaatg gacatactaa cgacaattaa attatttatc    60
atttaaaaag attaaatatt ttttcttaaa ttattcctgt gctttaaaat tcttaacaga   120
aaatttaaaa ttagacattt gtaccattag agaaaactg tgggactcat ttgtttatta    180
gattatttca gctagcaact gactctcttg tacatttcat ttttacattc ctttaattat   240
gcatcattaa cagtagtaga ttgcatctct taaaaaaaaa attagattgc agtattgcct   300
tggaaatatg gaattacaat gtcaaaatat tttaacgaat aacgatgcgt agcttaaagt   360
tcaagacaca attttaacgt tatatagtgc atcaatgttt gaaattttag tgtataaata   420
acgtattttt gataatattt tttacacaac aatcctctta aattttctta tcttatttca   480
tttaaccgtt ctcttaaatt gtcttatctt ttttacacac aaatgaatcc caataaacat   540
ggttgggatt tatttgagtt cttaacttta ggaaccaaat atataataat ttttttttt    600 taaaaaaaaa gagataaat atagaagaaa aggatgtgat aaaggcaaga gaagcgtgtg    660
aacaagagag agacgaatct aggtggattt gacgtacgtt gaatgaatgt tgaatataag   720
```

```
taataacgct gaggctgtag gtgtgggtaa taaaaaaaga gagaagccgc atcaacatca    780
tccaatatat ggacgttaaa agagcgtcgt aatccatttc catttctcat ctatcttcac    840
ttcctcgtcc tcatcctcat ccacctattc tcaacccaga cgcaatgccc atgtacactc    900
catcactctc cgcaccctcc tccaatcaca ttcaaccaag tgtcacactc cccttatata    960
tcacaaccac caagctcaat ctcaagcagc agcatcacac cacaccaatg ccaatcccca   1020
tgtgcaacga aattcaagcc caagcccaag cccaagccca agcccaacct gggtttaagc   1080
tcgtcggttt caaaaacttc gtccgaacca atcctaagtc ggaccgcttt caagtcaacc   1140
gcttccacca catcgagttc tggtgcaccg atgccaccaa cgcctctcgc cgattctctt   1200
ggggacttgg aatgcctatt gtggcaaaat ctgatctctc caccggaaac caaatccacg   1260
cctcctacct cctccgctcc ggcgacctct ccttcctctt ctccgctcct tactctccct   1320
ctctctccgc cggctcctcc gctgcctcct ccgcctccat tcccagtttc gacgccgcca   1380
cctgccttgc cttcgctgcc aaacacggct tcggcgtccg cgccatcgcc ttggaagtcg   1440
ccgacgcgga agccgctttc agcgccagcg tcgcgaaagg agccgagccg gcgtcgccgc   1500
cggttctcgt cgacgatcgc accggcttcg cggaggtgcg cctctacggc gacgtggtgc   1560
tccgctacgt cagctacaag gacgccgcgc cgcaggcgcc acacgcagat ccgtcgcggt   1620
ggttcctgcc gggattcgag gccgcggcgt cgtcgtcttc gtttccggag ctggactacg   1680
ggatccggcg gctggaccac gccgtcggga acgttccgga gctggcgccg gcggtgaggt   1740
acctgaaagg cttcagcgga ttccacgagt tcgcggagtt caccgcggag gacgtgggaa   1800
cgagcgagag cgggttgaac tcggtggttc tggcgaacaa ctcggagacg tgttgctgc    1860
cgctgaacga gccggtttac ggaacgaaga ggaagagcca gattgagacg tatttggaac   1920
acaacgaagg tgctggtgtg cagcaccttg cgcttgttac tcacgacatc ttcaccacac   1980
tgagagagat gagaaagcga agtttccttg gtggatttga gttcatgcct tctcctcctc   2040
ccacctatta cgccaacctc cacaaccgtg ccgctgatgt gttgaccgtt gaccagatta   2100
agcagtgtga ggagcttggg attcttgttg acagagatga tcagggcact ctgcttcaga   2160
ttttcaccaa gcctgttggg gacaggttct tcatttctg cttctttttt ttttgttttt    2220
ttaatccctg ctaaacaact ttattataac tctcacattc tattagccta gccttgatga   2280
cttttaattt acgttaaact gtgcttttta ttctcctact ttgttagttt ttttttttat    2340
ataaaatttt aattttcaa ttataacttt caataattaa caaatgatgt acagtatagt     2400
gttatgtcag aatggatgta cttgatgtag cagttcatca gagtgtttcc ctctacaaat   2460
tgtacttttg tcccttctcct gacataaagt ttacgacatt gaaaaaattg atagataaaa   2520
gtgcaattta tttatcttcc gctttgaact gattgaaagt ggtaaaagtt agattaacaa    2580
tttgacagtg tttgtgtgtt ggagggtggt gattagttaa atgtgttttg tgttgaattg    2640
acaggccaac gatattcata gagataattc agaggatcgg gtgcatggtg gaggatgagg   2700
aagggaaggt gtaccagaag ggtgcatgtg ggggttttgg gaaaggcaat tttctgagc    2760
ttttcaaatc cattgaagaa tatgagaaga ctttggaagc taaaagaacc gcgtaagcac   2820
attggaagaa cacaaatact cctttgttga aatgattaat gaggaatcaa tgtggcatag   2880
ggtgtttata ctctataata catagaatta caatgatagt gtcctcccett              2930
```

What which is claimed:

1. A method of conferring to a plant tolerance to an herbicide that is an inhibitor of 4-hydroxyphenylpyruvate dioxygenase (HPPD), said plant comprising an endogenous gene encoding an HPPD enzyme and said method comprising expressing in said plant a nucleic acid molecule comprising a nucleotide sequence encoding a transcription activator-like (TAL) effector, said TAL effector comprising a repeat domain that is engineered for recognition of a region of the endogenous promoter of said HPPD gene, whereby the TAL-effector is capable of increasing the expression of the enzyme from said gene, wherein increased expression of said enzyme in said plant increases its tolerance to said herbicide, wherein said nucleotide sequence is selected from the group consisting of SEQ ID NOs:2-4 and nucleotide sequences encoding the amino acid sequence set forth in any of SEQ ID NOs:6-8.

2. The method of claim 1, wherein said nucleotide sequence is selected from the group consisting of SEQ ID NO:4 and nucleotide sequences encoding the amino acid sequence set forth in SEQ ID NO:8.

3. A nucleic acid construct comprising a nucleotide sequence encoding an artificial TAL effector and being capable of expression in a plant comprising an endogenous gene encoding an HPPD enzyme, said TAL effector comprising a repeat domain that is engineered for recognition of a region of the endogenous promoter of said HPPD gene, whereby the TAL effector is capable of increasing the expression of said HPPD enzyme from said gene, wherein increased expression of said enzyme in said plant increases its tolerance to an HPPD inhibitor herbicide, wherein said nucleotide sequence is selected from the group consisting of SEQ ID NOs:2-4 and nucleotide sequences encoding the amino acid sequence set forth in any of SEQ ID NOs:6-8.

4. The nucleic acid construct of claim 3, wherein said nucleotide sequence is selected from the group consisting of SEQ ID NO:4 and nucleotide sequences encoding the amino acid sequence of SEQ ID NO:8.

5. A plant or a plant cell comprising the nucleic acid construct of claim 3 stably incorporated into its genome.

6. The plant of claim 5, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

7. A seed of the plant of claim 6, wherein said seed comprises the nucleic acid construct stably incorporated into its genome.

* * * * *